(12) United States Patent
Shiraishi et al.

(10) Patent No.: US 11,285,111 B2
(45) Date of Patent: Mar. 29, 2022

(54) PARTICLE-PRODUCING METHOD AND PARTICLE-PRODUCING APPARATUS

(71) Applicant: Ricoh Company, Ltd., Tokyo (JP)

(72) Inventors: Naoki Shiraishi, Kanagawa (JP); Tatsuru Moritani, Kanagawa (JP); Tadahiko Morinaga, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 16/268,518

(22) Filed: Feb. 6, 2019

(65) Prior Publication Data
US 2019/0247314 A1    Aug. 15, 2019

(30) Foreign Application Priority Data

Feb. 9, 2018 (JP) .............................. JP2018-021539
Dec. 25, 2018 (JP) .............................. JP2018-240573

(51) Int. Cl.
*A61K 9/16* (2006.01)
*A61K 31/155* (2006.01)
*A61K 31/55* (2006.01)
*G03G 9/087* (2006.01)
*G03G 9/08* (2006.01)

(52) U.S. Cl.
CPC .......... *A61K 9/1694* (2013.01); *A61K 9/1647* (2013.01); *A61K 31/155* (2013.01); *A61K 31/55* (2013.01); *G03G 9/0819* (2013.01); *G03G 9/08755* (2013.01)

(58) Field of Classification Search
None
See application file for complete search history.

(56) References Cited

U.S. PATENT DOCUMENTS

| | | | |
|---|---|---|---|
| 10,772,836 B2* | 9/2020 | Onoue | A61K 9/1694 |
| 2008/0286679 A1 | 11/2008 | Norikane et al. | |
| 2009/0042118 A1 | 2/2009 | Suzuki et al. | |
| 2009/0317735 A1 | 12/2009 | Ohtani et al. | |
| 2010/0055590 A1 | 3/2010 | Honda et al. | |
| 2011/0007116 A1 | 1/2011 | Ohgaki | |

(Continued)

FOREIGN PATENT DOCUMENTS

| | | |
|---|---|---|
| CN | 1119934 A | 4/1996 |
| CN | 1303275 A | 7/2001 |

(Continued)

OTHER PUBLICATIONS

Hiroki Suzuki, Tatsuru Moritani, Tadahiko Morinag, Yoshiki Seto, Hideyuki Sato, Satomi Onoue. "Amorphous solid dispersion of cyclosporine A prepared with fine droplet drying process: Physicochemical and pharmacokinetic characterization." International Journal of Pharmaceutics 519 (2017) 213-219. (Year: 2017).*

(Continued)

*Primary Examiner* — Isaac Shomer
(74) *Attorney, Agent, or Firm* — Xsensus LLP

(57) ABSTRACT

A particle-producing method is provided including the processes of: discharging a liquid from discharge holes provided on a liquid-storing unit storing the liquid to make the liquid into droplets, the liquid containing a physiologically active substance and a polymer; and solidifying the droplets into a particle.

15 Claims, 9 Drawing Sheets

(56) References Cited

U.S. PATENT DOCUMENTS

| | | | |
|---|---|---|---|
| 2012/0094231 A1 | 4/2012 | Norikane et al. | |
| 2012/0270147 A1 | 10/2012 | Katoh et al. | |
| 2013/0010035 A1 | 1/2013 | Norikane et al. | |
| 2013/0034810 A1 | 2/2013 | Norikane et al. | |
| 2013/0241983 A1 | 9/2013 | Aoki et al. | |
| 2013/0273188 A1 | 10/2013 | Takahashi et al. | |
| 2014/0038100 A1* | 2/2014 | Katoh | G03G 9/0802 430/137.1 |
| 2014/0097267 A1 | 4/2014 | Shitara et al. | |
| 2014/0141110 A1 | 5/2014 | Katoh et al. | |
| 2014/0242514 A1 | 8/2014 | Inoue et al. | |
| 2014/0292947 A1 | 10/2014 | Norikane et al. | |
| 2015/0108671 A1 | 4/2015 | Norikane et al. | |
| 2017/0050204 A1 | 2/2017 | Shitara et al. | |
| 2018/0085314 A1 | 3/2018 | Morinaga et al. | |
| 2019/0247314 A1* | 8/2019 | Shiraishi | A61K 31/155 |

FOREIGN PATENT DOCUMENTS

| | | | |
|---|---|---|---|
| CN | 106705574 A | 5/2017 | |
| EP | 0 275 834 A1 | 7/1988 | |
| JP | 60-100516 | 6/1985 | |
| JP | 1-115638 | 5/1989 | |
| JP | 8-281155 | 10/1996 | |
| JP | 2007-199463 | 8/2007 | |
| JP | 2008-292976 | 12/2008 | |
| JP | 2016-042424 * | 1/2017 | ........... A61K 9/1694 |
| JP | 2017-160188 | 9/2017 | |
| WO | 2017150692 A1 | 9/2017 | |
| WO | WO-2017150692 A1 * | 9/2017 | ........... A61K 9/1694 |

OTHER PUBLICATIONS

Chemical Book. "53902-17-3(TRANILAST) Product Description." https://www.chemicalbook.com/ChemicalProductProperty_US_CB3289228.aspx accessed Feb. 2, 2021, pp. 1-2. (Year: 2021).*

N Sandler, A Maattanen, P Ihalainen, L Kronberg, A Meierjohann, T Viitala, J Peltonen. "Inkjet Printing of Drug Substances and Use of Porous Substrates-Towards Individualized Dosing." Journal of Pharmaceutical Sciences, vol. 100, No. 8, Aug. 2011, pp. 3386-3395. (Year: 2011).*

Min Chen, Shuxue Zhou, Bo You, and Limin Wu. "A Novel Preparation Method of Raspberry-like PMMA/SiO2 Hybrid Microspheres." Macromolecules, vol. 38, 2005, pp. 6411-6417. (Year: 2005).*

U.S. Appl. No. 16/081,512, filed Mar. 2, 2017 Tatsuru Moritani, et al.

European Office Action dated Jul. 11, 2019, issued in corresponding European Application No. 19155608.3, 8 pages.

Hiroki Suzuki et al., "Amorphous solid dispersion of cyclosporine A prepared with fine droplet drying process: Physicochemical and pharmacokinetic characterization", International Journal of Pharmaceutics, Jan. 16, 2017, 7 pages.

Anonymous: "Printed-Droplet Drying Improves Drug Delivery", Jun. 19, 2017, 6 pages.

Office Action dated Jan. 18, 2021 in Chinese Patent Application No. 201910106013.X, 10 pages.

* cited by examiner

PARTICLE-PRODUCING METHOD AND PARTICLE-PRODUCING APPARATUS

CROSS-REFERENCE TO RELATED APPLICATIONS

This patent application is based on and claims priority pursuant to 35 U.S.C. § 119(a) to Japanese Patent Application Nos. 2018-021539 and 2018-240573, filed on Feb. 9, 2018 and Dec. 25, 2018, respectively, in the Japan Patent Office, the entire disclosure of each of which is incorporated by reference herein.

BACKGROUND

Technical Field

Embodiments of this disclosure relate to a particle-producing method and a particle-producing apparatus.

Description of the Related Art

Conventionally, pharmaceuticals such as tablets and capsules have been produced using a sustained-release particle containing a physiologically active substance such as a pharmaceutical compound in medical applications and the like.

For example, a method for producing a sustained-release particle containing a physiologically active substance through in-water drying, a method for producing a drug particle by spray-drying a liquid containing a physiologically active substance through spray drying, and the like have been proposed.

In addition, in attempting to improve properties such as particle handleability, elution rate, and elution rate unevenness, a method for producing a particle used for medicines and the like by inkjet discharging using a liquid column resonance has been proposed for pulverizing a particle and obtaining a particle having a narrow particle size distribution.

SUMMARY

In accordance with some embodiments of the present invention, a particle-producing method is provided. The method includes the processes of: discharging a liquid from discharge holes provided on a liquid-storing unit storing the liquid to make the liquid into droplets, where the liquid containing a physiologically active substance and a polymer; and solidifying the droplets into a particle.

In accordance with some embodiments of the present invention, a particle-producing apparatus is provided. The apparatus includes: a discharge device including a liquid-storing unit storing a liquid containing a physiologically active substance and a polymer, configured to discharge the liquid from discharge holes provided on the liquid-storing unit to make the liquid into droplets; and a solidification device configured to solidify the droplets into a particle. A content of the physiologically active substance in the particle is 25% by mass or more based on the mass of the particle, and the particle has a volume average particle diameter (Dv) of 12 μm to 100 μm and a particle size distribution (volume average particle diameter (Dv)/number average particle diameter (Dn)) of 1.00 to 1.50.

BRIEF DESCRIPTION OF THE DRAWINGS

A more complete appreciation of the disclosure and many of the attendant advantages and features thereof can be readily obtained and understood from the following detailed description with reference to the accompanying drawings, wherein.

Figure 1:
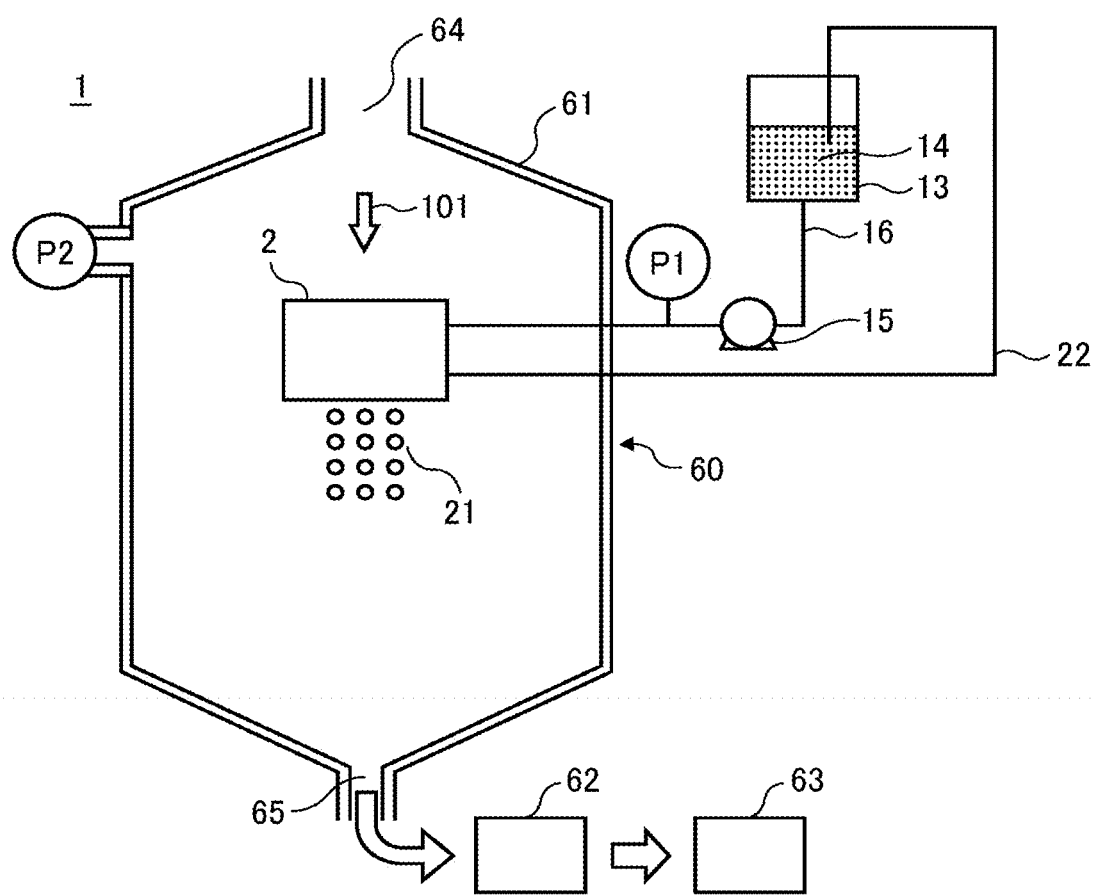
FIG. 1 is a schematic diagram illustrating a particle-producing apparatus according to an embodiment of the present invention.

The accompanying drawings are intended to depict embodiments of the present invention and should not be interpreted to limit the scope thereof. The accompanying drawings are not to be considered as drawn to scale unless explicitly noted.

DETAILED DESCRIPTION OF EMBODIMENTS

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Embodiments of the present invention are described in detail below with reference to accompanying drawings. In describing embodiments illustrated in the drawings, specific terminology is employed for the sake of clarity. However, the disclosure of this patent specification is not intended to be limited to the specific terminology so selected, and it is to be understood that each specific element includes all technical equivalents that have a similar function, operate in a similar manner, and achieve a similar result.

For the sake of simplicity, the same reference number will be given to identical constituent elements such as parts and materials having the same functions and redundant descriptions thereof omitted unless otherwise stated.

According to an embodiment of the present invention, a particle-producing method is provided that produces a particle containing a high concentration of physiologically active substance and allowing high precision control of sustained releasability of the particle.
(Particle-Producing Method and Particle-Producing Apparatus)

The particle-producing method of the present disclosure includes a discharge process of discharging a liquid from discharge holes provided on a liquid-storing unit storing the liquid to make the liquid into droplets, where the liquid contains a physiologically active substance and a polymer, and a solidification process of solidifying the droplets to produce a particle, and furthermore optionally includes other processes.

The particle-producing apparatus of the present disclosure includes a discharge device including a liquid-storing unit storing a liquid containing a physiologically active substance and a polymer, configured to discharge the liquid from discharge holes provided on the liquid-storing unit to make the liquid into droplets, and a solidification device configured to solidify the droplets to produce a particle, and furthermore optionally includes other devices.

The inventors of the present invention have studied a method for producing a sustained-release particle, and as a result, they have obtained the following findings.

In a technique described in JP-S60-100516-A, since water is used in a producing process, there are problems that a physiologically active substance in a particle is eluted, and a content of the physiologically active substance in the particle is decreased.

Additionally, in a technique described in JP-H08-281155-A, since a particle is produced by spray drying, there are problems that the obtained particle has a wide particle size distribution and a content of a physiologically active substance in the particle becomes uneven, and thus control of a sustained releasability is impossible. Furthermore, the particle produced by spray drying has problems that the physiologically active substance partially does not adsorb to the polymer and is atomized alone, which causes an initial burst, and control of the sustained releasability is impossible.

Furthermore, in a technique described in JP-2017-160188-A, since a diameter of a particle obtained by a liquid column resonance is too small, encapsulation of a physiologically active substance with a polymer in the particle is impossible, and thus acquisition of a sustained-release particle is impossible.

In the particle-producing method according to an embodiment of the present invention, the discharge process of discharging a liquid from discharge holes provided on a liquid-storing unit storing the liquid to make the liquid into droplets, where the liquid containing a physiologically active substance and a polymer, and the solidification process of solidifying the droplets are adopted. Thereby, the particle can be produced without using water, and the diameter of the particle to be produced can be increased and the particle size distribution of the particle can be narrowed without decreasing the content of the physiologically active substance contained in the particle. Thus, a particle having sustained releasability controlled with high precision can be obtained.

In the present disclosure, the "particle" is also referred to as "microcapsule" or "microparticle".
<Discharge Process and Discharge Device>

In the discharge process, the liquid containing the physiologically active substance and the polymer is discharged from the discharge holes provided on the liquid-storing unit storing the liquid to make the liquid into droplets. This process is performed by the discharge device.

Examples of the discharge device used in the discharge process include, but are not limited to, (1) a device employing a "volume-changing device" that changes the volume of the liquid-storing unit by vibration, (2) a device employing a "constricted part-generating device" that discharges the liquid from the plurality of discharge holes provided on the liquid-storing unit while vibrating the liquid-storing unit to make the liquid into droplets from a columnar state through a constricted state, and (3) a device using a "nozzle-vibrating device" that vibrates a thin film having a nozzle. Hereinafter, each device will be explained.
<<Volume-Changing Device>>

The volume-changing device is not particularly limited as long as the device can change the volume of the liquid-storing unit, and can be appropriately selected depending on the intended purpose. Examples of the volume-changing device include, but are not limited to, a piezoelectric element (also referred to as "piezoelement") that stretches and shrinks in response to a voltage, and an electrothermal conversion element such as a heating resistor.
<<Constricted Part-Generating Device>>

An example of the constricted part-generating device is a device using a technique described in JP-2007-199463-A. In JP-2007-199463-A, a liquid-storing unit is vibrated by a vibration device using a piezoelectric element in contact with a part of the liquid-storing unit, meanwhile a raw material liquid is discharged from a plurality of nozzle holes provided on the liquid-storing unit, and the raw material fluid is made into droplets from a columnar state through a constricted state.
<<Nozzle-Vibrating Device>>

The nozzle-vibrating device may use a technique described in JP-2008-292976-A. In JP-2008-292976-A, a thin film having a plurality of nozzles provided on a liquid-storing unit, and a piezoelectric element disposed around a deformable region of this thin film to vibrate the thin film are used to discharge a raw material liquid from the plurality of nozzles and make the liquid into droplets.

For generating vibration, a piezoelectric element is commonly used. The piezoelectric element is not particularly limited, and a shape, a size, and a material of the piezoelectric element can be appropriately selected depending on the intended purpose. For example, a piezoelectric element used in the conventional inkjet discharging method can be suitably used.

The shape and size of the piezoelectric element are not particularly limited, and can be appropriately selected depending on the shape or the like of the discharge hole.

The material of the piezoelectric element is not particularly limited, and can be appropriately selected depending on the intended purpose. Examples of the material include, but are not limited to, a piezoelectric ceramic such as lead zirconate titanate (PZT), a piezoelectric polymer such as polyvinylidene fluoride (PVDF), and a monocrystal such as quartz, $LiNbO_3$, $LiTaO_3$, and $KNbO_3$.

—Discharge Hole—

The discharge hole is not particularly limited, and can be appropriately selected depending on the intended purpose. Examples of the discharge hole include, but are not limited to, an opening provided on a nozzle plate A number, a sectional shape, and a size of the discharge holes can be appropriately selected.

The number of the discharge holes is not particularly limited, and can be appropriately selected depending on the intended purpose. For example, the number is preferably 2 to 3,000. When the number of the discharge holes is 2 to 3,000, the productivity can be improved.

The sectional shape of the discharge hole is not particularly limited, and can be appropriately selected depending on the intended purpose. Examples of the sectional shape include, but are not limited to, (1): a tapered shape such that an opening diameter of the discharge hole narrows from a liquid-contacting-face (inlet) of the discharge hole toward a liquid-discharging-face (outlet) of the discharge hole, (2): a shape such that the opening diameter narrows from the liquid-contacting-face (inlet) of the discharge hole toward the liquid-discharging-face (outlet) of the discharge hole while maintaining a round shape, (3): a shape such that the opening diameter narrows from the liquid-contacting-face (inlet) of the discharge toward the liquid-discharging-face (outlet) of the discharge hole while maintaining a certain nozzle angle, and (4): a combination of the shape (1) and the shape (2). Especially, (3): the shape such that the opening diameter narrows from the liquid-contacting-face (inlet) of the discharge hole toward the liquid-discharging-face (outlet) of the discharge hole while maintaining a certain nozzle angle is preferable for maximizing a pressure applied to the liquid at the discharge hole.

The nozzle angle in the shape (3) is not particularly limited, and can be appropriately selected depending on the intended purpose. However, the nozzle angle is preferably 60° to 90°. When the nozzle angle is 60° or larger, it is much easier to apply pressure to the liquid, and further it becomes easy to process the discharge hole. When the nozzle angle is 90° or smaller, a pressure is applied to the discharge hole, and thus discharge of the droplets can be stabilized. Thus, the maximum value of the nozzle angle is preferably 90°.

The size of the discharge hole can be appropriately selected in consideration of the sustained releasability of the particle to be produced. For example, the diameter of the discharge hole is preferably 12 μm to 100 μm, and more preferably 15 μm to 30 μm. When the size of the discharge hole is 12 μm to 100 μm, a particle having a particle diameter sufficient to exhibit the sustained releasability can be obtained.

<<Liquid-storing Unit>>

The liquid-storing unit is not particularly limited as long as the unit has a space for temporarily storing the stored liquid containing the physiologically active substance and the polymer. A shape, a size, and the like can be appropriately selected depending on the intended purpose.

—Liquid—

The liquid contains the physiologically active substance and the polymer, and furthermore optionally a dispersant, a solvent, and other components.

—Physiologically Active Substance—

The physiologically active substance is not particularly limited, and can be appropriately selected depending on the intended purpose. The same physiologically active substance as that contained in the particle of the present disclosure described later can be suitably used.

—Polymer—

The polymer is not particularly limited, and can be appropriately selected depending on the intended purpose. The same polymer as that contained in the particle of the present disclosure described later can be suitably used.

—Dispersant—

The dispersant can be suitably used for dispersing the physiologically active substance. When the physiologically active substance is uniformly dispersed in the liquid, the physiologically active substance can be encapsulated in the particle so that the physiologically active substance remains in a solid state.

The dispersant may be a low molecular weight dispersant or a high molecular weight dispersant polymer.

The low molecular weight dispersant refers to a compound having a weight average molecular weight of less than 15,000. The high molecular weight dispersant polymer refers to a compound having repeating covalent bonds between one or more monomers and having a weight average molecular weight of 15,000 or more.

The low molecular weight dispersant is not particularly limited as long as the dispersant is acceptable as a physiologically active substance such as a medicine, and can be appropriately selected depending on the intended purpose. Examples of the low molecular weight dispersant include, but are not limited to, a lipid, a saccharide, a cyclodextrin, an amino acid, and an organic acid. These may be used alone or in combination.

The lipid is not particularly limited, and can be appropriately selected depending on the intended purpose. Examples of the lipid include, but are not limited to, a medium- or long-chain monoglyceride, diglyceride or triglyceride, a phospholipid, a vegetable oil (e.g. soybean oil, avocado oil, squalene oil, sesame oil, olive oil, corn oil, rapeseed oil, safflower oil, sunflower oil), a fish oil, a seasoning oil, a water-insoluble vitamin, a fatty acid, and a mixture thereof, as well as a derivative thereof. These may be used alone or in combination.

The saccharide is not particularly limited, and can be appropriately selected depending on the intended purpose. Examples of the saccharide include, but are not limited to, glucose, mannose, idose, galactose, fucose, ribose, xylose, lactose, sucrose, maltose, trehalose, turanose, raffinose, maltotriose, acarbose, glycerin, sorbitol, lactitol, maltitol, mannitol, xylitol, erythritol, polyol, and a derivative thereof. These may be used alone or in combination.

The cyclodextrin is not particularly limited, and can be appropriately selected depending on the intended purpose. Examples of the cyclodextrin include, but are not limited to, hydroxypropyl-β-cyclodextrin, β-cyclodextrin, γ-cyclodextrin, α-cyclodextrin, and cyclodextrin derivatives. These may be used alone or in combination.

The amino acid is not particularly limited, and can be appropriately selected depending on the intended purpose. Examples of the amino acid include, but are not limited to, valine, lysine, leucine, threonine, isoleucine, asparagine, glutamine, phenylalanine, aspartic acid, serine, glutamic acid, methionine, arginine, glycine, alanine, tyrosine, proline, histidine, cysteine, tryptophan, and a derivative thereof. These may be used alone or in combination.

The organic acid is not particularly limited, and can be appropriately selected depending on the intended purpose. Examples of the organic acid include, but are not limited to, adipic acid, ascorbic acid, citric acid, fumaric acid, gallic acid, glutaric acid, lactic acid, malic acid, maleic acid, succinic acid, tartaric acid, and a derivative thereof. These may be used alone or in combination.

The high molecular weight dispersant polymer is not particularly limited, and can be appropriately selected depending on the intended purpose. Examples of the high molecular weight dispersant polymer include, but are not limited to, water-soluble cellulose, polyalkylene glycol, poly(meth)acrylamide, poly(meth)acrylic acid, poly (meth)acrylate, polyallylamine, polyvinylpyrrolidone, polyvinyl alcohol, polyvinyl acetate, biodegradable polyester, polyglycolic acid, polyamino acid, gelatin, polymalic acid, polydioxanone, and a derivative thereof. These may be used alone or in combination.

The water-soluble cellulose is not particularly limited, and can be appropriately selected depending on the intended purpose. Examples of the water-soluble cellulose include, but are not limited to, an alkyl cellulose such as methyl cellulose and ethyl cellulose; a hydroxyalkyl cellulose such as hydroxyethyl cellulose and hydroxypropyl cellulose; and a hydroxyalkylalkyl cellulose such as hydroxyethylmethyl cellulose and hydroxypropylmethyl cellulose. These may be used alone or in combination. Especially, hydroxypropyl cellulose and hydroxypropylmethyl cellulose are preferable, and hydroxypropyl cellulose is more preferable, for improving solubility.

As the hydroxypropyl cellulose, various products having different viscosities varied depending on the weight average molecular weight, the substitution degree, and the molecular weight are commercially available from various companies. Any of the products can be used in the present disclosure.

The weight average molecular weight of the hydroxypropyl cellulose is not particularly limited, and can be appropriately selected depending on the intended purpose, but is preferably 15,000 to 400,000. For example, the weight average molecular weight can be measured by gel permeation chromatography (GPC).

A viscosity of an aqueous solution containing 2% by mass of hydroxypropyl cellulose (20 degrees C.) is not particularly limited, and can be appropriately selected depending on the intended purpose, but is preferably 2.0 mPa·s (centipoise, cps) to 4,000 mPa·s (centipoise, cps).

As the hydroxypropyl cellulose, a commercially available product can be used. The commercially available product of hydroxypropyl cellulose is not particularly limited, and can be appropriately selected depending on the intended purpose. Example of the commercially available product include, but are not limited to, HPC-SSL having a molecular weight of 15,000 to 30,000 and a viscosity of 2.0 mPa·s to 2.9 mPa·s, HPC-SL having a molecular weight of 30,000 to 50,000 and a viscosity of 3.0 mPa·s to 5.9 mPa·s, HPC-L having a molecular weight of 55,000 to 70,000 and a viscosity of 6.0 mPa·s to 10.0 mPa·s, HPC-M having a molecular weight of 110,000 to 150,000 and a viscosity of 150 mPa·s to 400 mPa·s, and HPC-H having a molecular weight of 250,000 to 400,000 and a viscosity of 1,000 mPa·s to 4,000 mPa·s (manufactured by NIPPON SODA CO., LTD.). These may be used alone or in combination. Especially, HPC-SSL having a molecular weight of 15,000 to 30,000 and a viscosity of 2.0 mPa·s to 2.9 mPa·s is preferable.

The polyalkylene glycol is not particularly limited, and can be appropriately selected depending on the intended purpose. Examples of the polyalkylene glycol include, but are not limited to, polyethylene glycol (PEG), polypropylene glycol, polybutylene glycol, and a copolymer thereof. These may be used alone or in combination.

The poly(meth)acrylamide is not particularly limited, and can be appropriately selected depending on the intended purpose. Examples of the poly(meth)acrylamide include, but are not limited to, N-methyl(meth)acrylamide, N-ethyl(meth)acrylamide, N-propyl(meth)acrylamide, N-butyl(meth)acrylamide, N-benzyl(meth)acrylamide, N-hydroxyethyl(meth)acryl amide, N-phenyl(meth)acrylamide, N-tolyl(meth)acrylamide, N-(hydroxyphenyl)(meth)acrylamide, N-(sulfamoylphenyl)(meth)acrylamide, N-(phenyl sulfonyl)(meth)acrylamide, N-(tolyl sulfonyl)(meth)acrylamide, N,N-dimethyl(meth)acrylamide, N-methyl-N-phenyl(meth)acrylamide, and N-hydroxyethyl-N-methyl(meth)acrylamide. These may be used alone or in combination.

The poly(meth)acrylic acid is not particularly limited, and can be appropriately selected depending on the intended purpose. Examples of the poly(meth)acrylic acid include, but are not limited to, a homopolymer such as polyacrylic acid and polymethacrylic acid, and a copolymer such as an acrylic acid-methacrylic acid copolymer. These may be used alone or in combination.

The poly(meth)acrylate is not particularly limited, and can be appropriately selected depending on the intended purpose. Examples of the poly(meth)acrylate include, but are not limited to, ethyleneglycol di(meth)acrylate, diethyleneglycol di(meth)acrylate, propyleneglycol di(meth)acrylate, glycerol poly(meth)acrylate, polyethylene glycol (meth)acrylate, trimethylolpropane tri(meth)acrylate, pentaerythritol tetra(meth)acrylate, and 1,3-butyleneglycol di(meth)acrylate.

The polyallylamine is not particularly limited, and can be appropriately selected depending on the intended purpose. Examples of the polyallylamine include, but are not limited to, diallylamine and triallylamine. These may be used alone or in combination.

As the polyvinylpyrrolidone, a commercially available product can be used. The commercially available product of the polyvinylpyrrolidone is not particularly limited, and can be appropriately selected depending on the intended purpose. Examples of the product include, but are not limited to, Plasdone C-15 (manufactured by ISP Inc.), Kollidon VA64, Kollidon K-30, Kollidon CL-M (manufactured by Kawarlal & Co.), and Kollicoat TR (manufactured by BASF SE). These may be used alone or in combination.

The polyvinyl alcohol is not particularly limited, and can be appropriately selected depending on the intended purpose. Examples of the polyvinyl alcohol include, but are not limited to, a silanol-modified polyvinyl alcohol, a carboxyl-modified polyvinyl alcohol, and an acetoacetyl-modified polyvinyl alcohol. These may be used alone or in combination.

The polyvinyl acetate is not particularly limited, and can be appropriately selected depending on the intended purpose. Examples of the polyvinyl acetate include, but are not limited to, a vinyl acetate-crotonic acid copolymer and a vinyl acetate-itaconic acid copolymer. These may be used alone or in combination.

The biodegradable polyester is not particularly limited, and can be appropriately selected depending on the intended purpose. Examples of the biodegradable polyester include, but are not limited to, polylactic acid, poly-ε-caprolactone, succinate-based polymer, and polyhydroxyalkanoate. These may be used alone or in combination.

The succinate-based polymer is not particularly limited, and can be appropriately selected depending on the intended purpose. Examples of the succinate-based polymer include, but are not limited to, polyethylene succinate, polybutylene succinate, and polybutylene succinate adipate. These may be used alone or in combination.

The polyhydroxyalkanoate is not particularly limited, and can be appropriately selected depending on the intended purpose. Examples of the polyhydroxyalkanoate include, but are not limited to, polyhydroxypropionate, polyhydroxybutyrate, and polyhydroxyvalerate. These may be used alone or in combination.

The polyglycolic acid is not particularly limited, and can be appropriately selected depending on the intended purpose. Examples of the polyglycolic acid include, but are not limited to, a lactic acid-glycolic acid copolymer, a glycolic acid-caprolactone copolymer, and a glycolic acid-trimethylene carbonate copolymer. These may be used alone or in combination.

The polyamino acid is not particularly limited, and can be appropriately selected depending on the intended purpose. Examples of the polyamino acid include, but are not limited to, an amino acid homopolymer such as poly-α-glutamic acid, poly-γ-glutamic acid, polyaspartic acid, polylysine, polyarginine, polyornithine, and polyserine, and a copolymer thereof. These may be used alone or in combination.

The gelatin is not particularly limited, and can be appropriately selected depending on the intended purpose. Examples of the gelatin include, but are not limited to, a lime-treated gelatin, an acid-treated gelatin, a hydrolyzed gelatin, an enzyme-dispersed gelatin, and a derivative thereof. These may be used alone or in combination.

A natural dispersant polymer used for the gelatin derivative is not particularly limited, and can be appropriately selected depending on the intended purpose. Examples of the natural dispersant polymer include, but are not limited to, a protein, a polysaccharide, and a nucleic acid. The natural dispersant polymers also include a copolymer composed of a natural dispersant polymer and a synthetic dispersant polymer. These may be used alone or in combination.

The gelatin derivative refers to a gelatin derivatized by covalently bonding a hydrophobic group to a gelatin molecule. The hydrophobic group is not particularly limited, and can be appropriately selected depending on the intended purpose. Examples of the hydrophobic group include, but are not limited to, a polyester such as polylactic acid, polyglycolic acid, and poly-ε-caprolactone; a lipid such as cholesterol and phosphatidylethanolamine; an aromatic group having an alkyl group or a benzene ring; a heteroaromatic group; and a mixture thereof.

The protein is not particularly limited, and can be appropriately selected depending on the intended purpose. Examples of the protein include, but are not limited to, collagen, fibrin, and albumin. These may be used alone or in combination.

The polysaccharide is not particularly limited, and can be appropriately selected depending on the purpose. Examples of the polysaccharide include, but are not limited to, chitin, chitosan, hyaluronic acid, alginic acid, starch, and pectin. These may be used alone or in combination.

A content of the dispersant is preferably 5% by mass to 95% by mass, more preferably 50% by mass to 95% by mass, based on the total amount of the particle according to the present embodiment. When the content of the dispersant is 5% by mass to 95% by mass, the dose of the dispersant as a pharmaceutical composition is appropriate and the pharmaceutical components can be easily re-dispersed in water by the action of the dispersant, which is advantageous.

—Solvent—

The solvent is not particularly limited, and can be appropriately selected depending on the intended purpose. However, a solvent capable of dissolving or dispersing a slightly water-soluble compound or a pharmaceutically acceptable salt thereof is preferable.

Examples of the solvent include, but are not limited to, an aliphatic halogenated hydrocarbon (e.g. dichloromethane, dichloroethane, chloroform), an alcohol (e.g. methanol, ethanol, propanol), a ketone (e.g. acetone, methyl ethyl ketone), an ether (e.g. diethyl ether, dibutyl ether, 1,4-dioxane), an aliphatic hydrocarbon (e.g. n-hexane, cyclohexane, n-heptane), an aromatic hydrocarbon (e.g. benzene, toluene, xylene), an organic acid (e.g. acetic acid, propionic acid), an ester (e.g. ethyl acetate), and an amide (e.g. dimethylformamide, dimethylacetamide). These may be used alone or in combination. Especially, the aliphatic halogenated hydrocarbon, the alcohol, the ketone, and a mixed solvent thereof are preferable, and dichloromethane, 1,4-dioxane, methanol, ethanol, acetone, and a mixed solvent thereof are more preferable for solubility.

A content of the solvent is preferably 70% by mass to 99.5% by mass, more preferably 90% by mass to 99% by mass, based on the total amount of the liquid of the present embodiment. When the content of the solvent is 70% by mass to 99.5% by mass, there is an advantage in production stability in view of the solubility of the material and the viscosity of the solution.

—Other Components—

The other components are not particularly limited, and can be appropriately selected depending on the intended purpose. However, the components conventionally usable for medicines are preferable.

Examples of other components include, but are not limited to, water, an excipient, a flavor improver, a disintegrator, a fluidizer, an adsorbent, a lubricant, an odor improver, a surfactant, a fragrance, a colorant, an antioxidant, a masking agent, an antistatic agent, and a wetting agent. These may be used alone or in combination.

The excipient is not particularly limited, and can be appropriately selected depending on the intended purpose. Examples of the excipient include, but are not limited to, lactose, sucrose, mannitol, glucose, fructose, maltose, erythritol, maltitol, xylitol, palatinose, trehalose, sorbitol, crystalline cellulose, talc, silicic anhydride, calcium phosphate anhydride, precipitated calcium carbonate, and calcium silicate. These may be used alone or in combination.

The flavor improver is not particularly limited, and can be appropriately selected depending on the intended purpose. Examples of the flavor improver include, but are not limited to, L-menthol, white sugar, D-sorbitol, xylitol, citric acid, ascorbic acid, tartaric acid, malic acid, aspartame, acesulfame potassium, thaumatin, saccharin sodium, glycyrrhizin dipotassium, sodium glutamate, sodium 5'-inosinate, and sodium 5'-guanylate. These may be used alone or in combination.

The disintegrator is not particularly limited, and can be appropriately selected depending on the intended purpose. Examples of the disintegrator include, but are not limited to, lowly-substituted hydroxypropylcellulose, carmellose, carmellose calcium, carboxymethyl starch sodium, croscarmellose sodium, crospovidone, hydroxypropyl starch, and corn starch. These may be used alone or in combination.

The fluidizer is not particularly limited, and can be appropriately selected depending on the intended purpose. Examples of the fluidizer include, but are not limited to, light silicic anhydride, hydrated silicon dioxide, and talc. These may be used alone or in combination.

As the light silicic anhydride, a commercially available product can be used. The commercially available light silicic anhydride is not particularly limited, and can be appropriately selected depending on the intended purpose. Examples of the commercially available light silicic anhydride include, but are not limited to, Adsolider 101 (manufactured by Freund Corporation, average pore diameter: 21 nm).

As the adsorbent, a commercially available product can be used. The commercially available adsorbent is not particularly limited, and can be appropriately selected depending on the intended purpose. Examples of the commercially available adsorbent include, but are not limited to, Carplex (registered trademark of DSL. Japan Co., Ltd., component name: synthetic silica), Aerosil (registered trademark of NIPPON AEROSIL CO., LTD.) 200 (component name: hydrophilic fumed silica), Sylysia (registered trademark of FUJI SILYSIA CHEMICAL LTD., component name: amorphous silicon dioxide), and Alcamac (registered trademark of Kyowa Chemical Industry Co., Ltd., component name: synthetic hydrotalcite). These may be used alone or in combination.

The lubricant is not particularly limited, and can be appropriately selected depending on the intended purpose. Examples of the lubricant include, but are not limited to, magnesium stearate, calcium stearate, sucrose fatty acid ester, sodium stearyl fumarate, stearic acid, polyethylene glycol, and talc. These may be used alone or in combination.

The odor improver is not particularly limited, and can be appropriately selected depending on the intended purpose. Examples of the odor improver include, but are not limited to, trehalose, malic acid, maltose, potassium gluconate, anise refined oil, vanilla refined oil, and cardamom refined oil. These may be used alone or in combination.

The surfactant is not particularly limited, and can be appropriately selected depending on the intended purpose. Examples of the surfactant include, but are not limited to, polysorbate such as polysorbate 80; polyoxyethylene/polyoxypropylene copolymer; and sodium lauryl sulfate. These may be used alone or in combination.

The fragrance is not particularly limited, and can be appropriately selected depending on the intended purpose. Examples of the fragrance include, but are not limited to, lemon oil, orange oil, and peppermint oil. These may be used alone or in combination.

The colorant is not particularly limited, and can be appropriately selected depending on the intended purpose. Examples of the colorant include, but are not limited to, titanium oxide, Food Yellow No. 5, Food Blue No. 2, iron sesquioxide, and yellow iron sesquioxide. These may be used alone or in combination.

The antioxidant is not particularly limited, and can be appropriately selected depending on the intended purpose. Examples of the antioxidant include, but are not limited to, sodium ascorbate, L-cysteine, sodium sulfite, and vitamin E. These may be used alone or in combination.

The masking agent is not particularly limited, and can be appropriately selected depending on the intended purpose. Examples of the masking agent include, but are not limited to, titanium oxide. These may be used alone or in combination.

The antistatic agent is not particularly limited, and can be appropriately selected depending on to the intended purpose. Examples of the antistatic agent include, but are not limited to, talc and titanium oxide. These may be used alone or in combination.

The wetting agent is not particularly limited, and can be appropriately selected depending on the intended purpose. Examples of the wetting agent include, but are not limited to, polysorbate 80, sodium lauryl sulfate, sucrose fatty acid ester, macrogol, and hydroxypropylcellulose (HPC). These may be used alone or in combination.

The liquid may be free of a solvent as long as the liquid is in a state in which the physiologically active substance is dissolved, a state in which the physiologically active substance is dispersed, or a liquid state under a discharge condition. The liquid may also be in a state in which the particle component is melted.

<Solidification Process and Solidification Device>

The solidification process is a process of solidifying droplets and performed by a solidification device.

The solidification device is not particularly limited as long as the device can solidify droplets (put droplets into a solid state), and can be appropriately selected depending on the intended purpose. For example, when the liquid is prepared by dissolving or dispersing a solid raw material in a volatile solvent, the solidification device may employ a method for drying the droplets in which the droplets are jetted to a transporting air flow.

The method for drying the droplets using the transporting air flow is not particularly limited, and can be appropriately selected depending on the intended purpose. For example, a method in which a transporting direction of the transporting air flow is made substantially perpendicular to a droplet discharging direction is preferable. Incidentally, the method of drying using the transporting air flow will be explained in detail later with reference to the drawings.

For drying the solvent, a temperature, a vapor pressure, a gas type, and the like of the transporting air flow are preferably adjusted.

In addition, the particle is not necessarily completely dried as long as the collected particle remains in a solid state. In this case, another drying process may be added after collection.

In addition to this method, a method for drying droplets by utilizing temperature change or chemical change may be used.

<Other Processes>

Other processes are not particularly limited, and can be appropriately selected depending on the intended purpose. Examples of the other process include, but are not limited to, a particle collecting process.

The particle collecting process is a process of collecting the dried particle, and can be suitably performed by a particle-collecting device.

The particle-collecting device is not particularly limited, and can be appropriately selected depending on the intended purpose. Examples of the device include, but are not limited to, a cyclone collector and a back filter.

In the particle-producing method and the particle-producing apparatus of the present embodiment, the droplets are discharged using the discharge device that makes the liquid into droplets by discharging the liquid utilizing vibration. Thus, the sizes of the discharged droplets can be readily controlled, and the particle diameter of the particle can be increased and the particle size distribution can be narrowed. Consequently, a particle allowing high precision control of the sustained releasability of the particle can be produced.

Herein, an example of the particle-producing apparatus used in the particle-producing method of the present disclosure will be explained with reference to FIG. 1 to FIG. 4.

Figure 2:
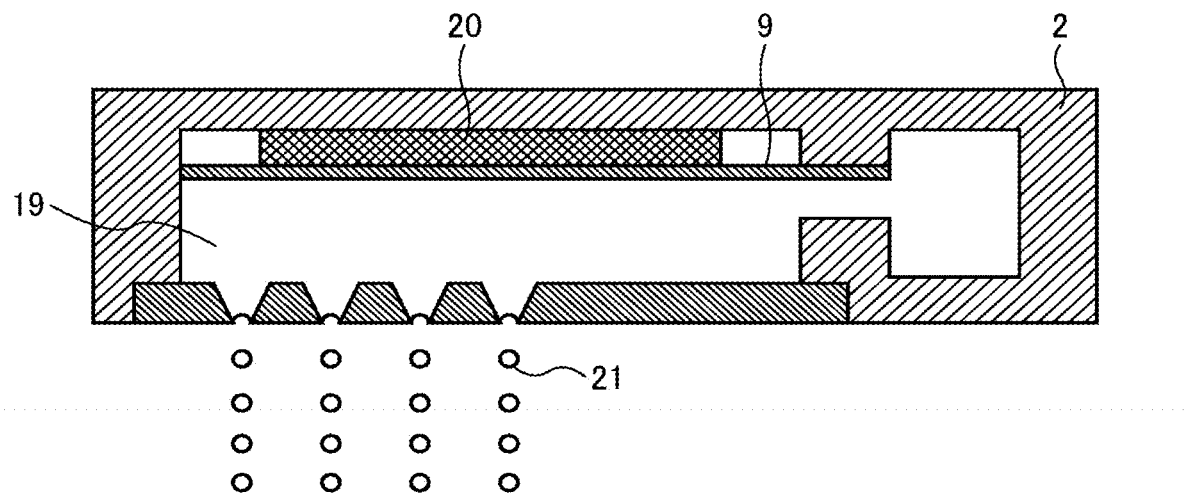
FIG. 2 is a schematic diagram illustrating an example of a droplet-discharging device using a volume-changing device, used in the particle-producing apparatus illustrated in FIG. 1.
Figure 3:
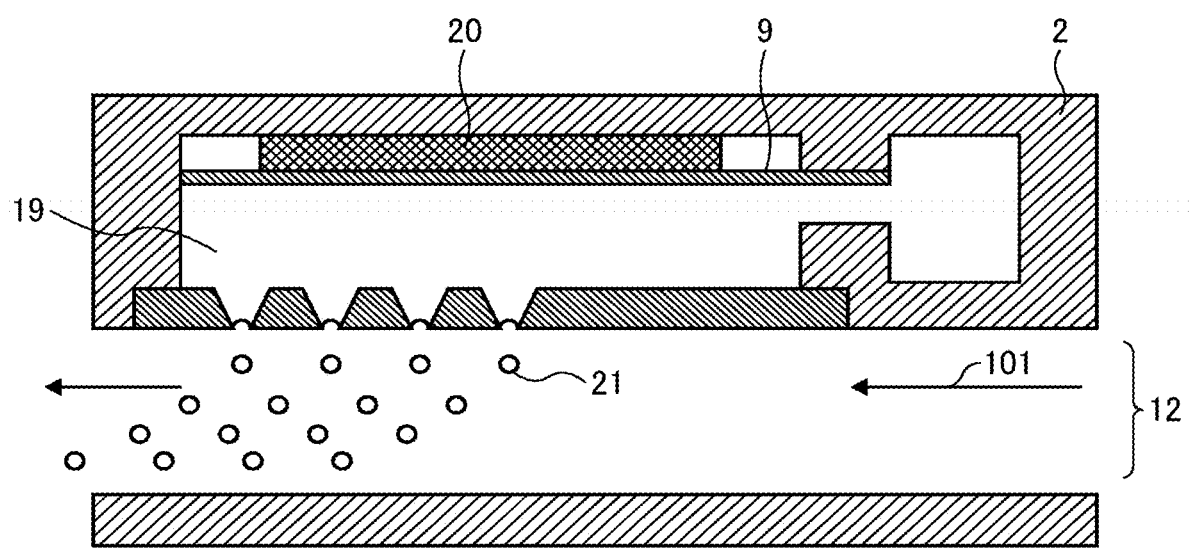
FIG. 3 is a schematic diagram illustrating another example of the droplet-discharging device using a volume-changing device, used in the particle-producing apparatus illustrated in FIG. 1.
Figure 4:
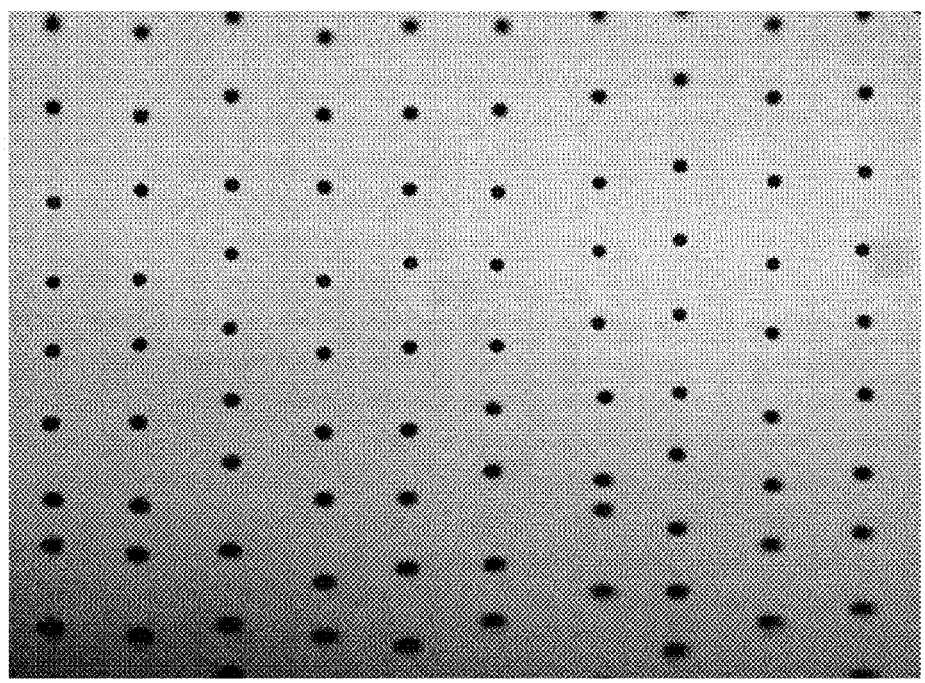
FIG. 4 is a schematic diagram illustrating discharge holes on the droplet-discharging device using the volume-changing device, used in the particle-producing apparatus illustrated in FIG. 1.

FIG. 1 is a schematic diagram illustrating an example of the particle-producing apparatus. FIG. 2 is a diagram illustrating an example of a droplet-discharging device used in the particle-producing apparatus. FIG. 3 is a diagram illustrating another example of a droplet-discharging device used in the particle-producing apparatus. FIG. 4 is a diagram illustrating an example of discharge holes of the discharge device used in the particle-producing apparatus.

A particle-producing apparatus 1 presented in FIG. 1 includes a droplet-discharging device 2, a drying collection unit 60, a transporting air flow outlet 65, and a particle-storing unit 63. The droplet-discharging device 2 is coupled to a raw material stored container 13 storing a liquid 14, and a liquid circulation pump 15. The liquid circulation pump 15 is configured to supply the liquid 14 stored in the raw material stored container 13 to the droplet-discharging device 2 through a liquid supply tube 16, and to pump the liquid 14 inside the liquid supply tube 16 to return the liquid 14 to the raw material stored container 13 through a liquid return tube 22. The liquid 14 can be supplied to the droplet-discharging device 2 at any time. A pressure gauge P1 is disposed to the liquid supply tube 16, and a pressure gauge P2 is disposed to the drying collection unit 60. A pressure for supplying the liquid 14 to the droplet-discharging device 2 and a pressure inside the drying collection unit 60 are managed by the pressure gauges P1 and P2. At this time, if the pressure measurement value of the P1 is higher than the pressure measurement value of the P2, the liquid 14 may ooze out from the discharge holes. If the pressure measurement value of the P1 is lower than the pressure measurement value of the P2, gas may enter the droplet-discharging device 2, and the discharge may be stopped. Thus, it is preferable that the pressure measurement value of the P1 and the pressure measurement value of the P2 are substantially the same.

Inside a chamber 61, a downdraft (transporting air flow) 101 is formed from a transporting air flow inlet 64. Droplets 21 discharged from the droplet-discharging device 2 are transported downwards not only by gravity but also by the transporting air flow 101, are discharged from the transporting air flow outlet 65, are collected by a particle-collecting device 62, and then are stored in the particle-storing unit 63.

Additionally, in the droplet-discharging process, when the discharged droplets are brought contact with each other before drying, the droplets unite with each other to form one particle (hereinafter, this phenomenon is also referred to as "coalescence" in some cases). For obtaining a particle having a uniform particle diameter distribution, distances among discharged droplets should be maintained. The jetted droplets have a certain initial speed for traveling, but the traveling speed eventually decreases due to air resistance. Droplets jetted later may catch up with the droplets traveling at the decreased speed, and as a result, coalescence occurs. Since this phenomenon occurs regularly, a particle diameter distribution is considerably poor when the particle formed of such droplets is collected. For preventing the coalescence, it is preferable that reduction in the speed of the droplets is prevented by transporting and drying the droplets by the transporting air flow 101 so as not to bring the droplets into contact with each other, and eventually, fine particles are transported to the particle-collecting device 62.

As illustrated in FIG. 1, part of the transporting air flow 101 may be positioned as a first airflow near the droplet-discharging device 2 in the same direction as the droplet-discharging direction. This configuration can prevent the coalescence by preventing slowing of the speed of the droplets immediately after the droplets are discharged.

FIG. 2 is an enlarged view of the droplet-discharging device in the particle-producing apparatus in FIG. 1. As illustrated in FIG. 2, the droplet-discharging device 2 includes a volume-changing device 20, an elastic plate 9, and a liquid-storing unit 19. When a voltage is applied to the volume-changing device 20, the droplet-discharging device 2 is deformed to decrease the volume of the liquid-storing unit 19, and thus the droplet-discharging device 2 discharges the liquid stored in the liquid-storing unit 19 as the droplets from the discharge holes.

FIG. 3 is a diagram illustrating another aspect of the droplet-discharging device in the particle-producing apparatus. As illustrated in FIG. 3, in an air flow passage 12, the transporting air flow 101 may be directed substantially perpendicular to the discharge direction. Although not illustrated, the transporting air flow 101 may be angled. The direction of the transporting air flow 101 is preferably angled in a manner that droplets come away from the droplet-discharging device 2. As illustrated in FIG. 3, the volume-changing device 20 changes the volume of the liquid-storing unit 19 through the elastic plate 9 to discharge the droplets 21, and the transporting air flow 101 for preventing the coalescence is supplied from a direction substantially perpendicular to the discharged droplets 21. In this case, it is preferable that the discharge holes are arranged so that trajectories of the droplets 21 discharged from the discharge holes and transported by the transporting air flow 101 are prevented from overlapping with each other for preventing the coalescence, as illustrated in FIG. 4.

After preventing the coalescence by the first air flow as described above, the dried particle may be transported to the particle-collecting device by a second air flow.

The speed of the first air flow is preferably equal to or larger than the discharge speed of the droplets. If the speed of the transporting air flow 101 for preventing the coalescence is smaller than the discharge speed of the droplets, it may be difficult to exhibit the function of preventing contact between the droplets 21, which is the original object of the transporting air flow for preventing the coalescence.

The first air flow may have any additional property for preventing coalescence of the droplets 21. The properties of the first air flow does not have to be identical to those of the second air flow. Moreover, a chemical substance which accelerates drying of the surface of the particle may be mixed in the transporting air flow for preventing the coalescence, or a chemical substance expected to have a physical effect may be added.

The transporting air flow 101 is not particularly limited in terms of a state of the air flow. The transporting air flow 101 may be laminar flow, swirling flow, or turbulence. The type of the gas constituting the transporting air flow 101 is not particularly limited, and can be appropriately selected depending on the intended purpose. Air, or an incombustible gas such as nitrogen may be used. Moreover, a temperature of the transporting air flow 101 can be appropriately adjusted. Preferably, the temperature does not change during production. In addition, a device configured to change the airflow condition of the transporting air flow 101 may be disposed in the chamber 61. The transporting air flow 101 may be used for not only preventing coalescence of the droplets 21 but also preventing deposition of the droplets to the chamber 61.

When an amount of the residual solvent contained in the particle collected by the particle-collecting device 62 illustrated in FIG. 1 is great, it is preferable that the secondary drying is optionally performed in order to reduce the amount of the residual solvent. The secondary drying can be performed by means of typical drying known in the art, such as fluidized-bed drying and vacuum drying. Remaining of the solvent in the particle causes not only temporal change of the particle properties such as heat-resistant preservability, fixity, and charging characteristic, but also volatilization of the solvent during heat fixing. Thereby, a possibility of harmful influence on users and peripheral equipment is increased, and thus it is preferable to sufficiently dry the particle.

If the amount of the residual solvent contained in the obtained particle is great, it is preferable to optionally perform the secondary drying. The secondary drying can be performed by means of typical drying known in the art, such as fluidized-bed drying and vacuum drying.

When the solvent remains in the produced particle, the particle properties such as heat-resistant preservability, fixity, and charging characteristic may change over time, and thus it is preferable to sufficiently dry the particle.

Figure 5:
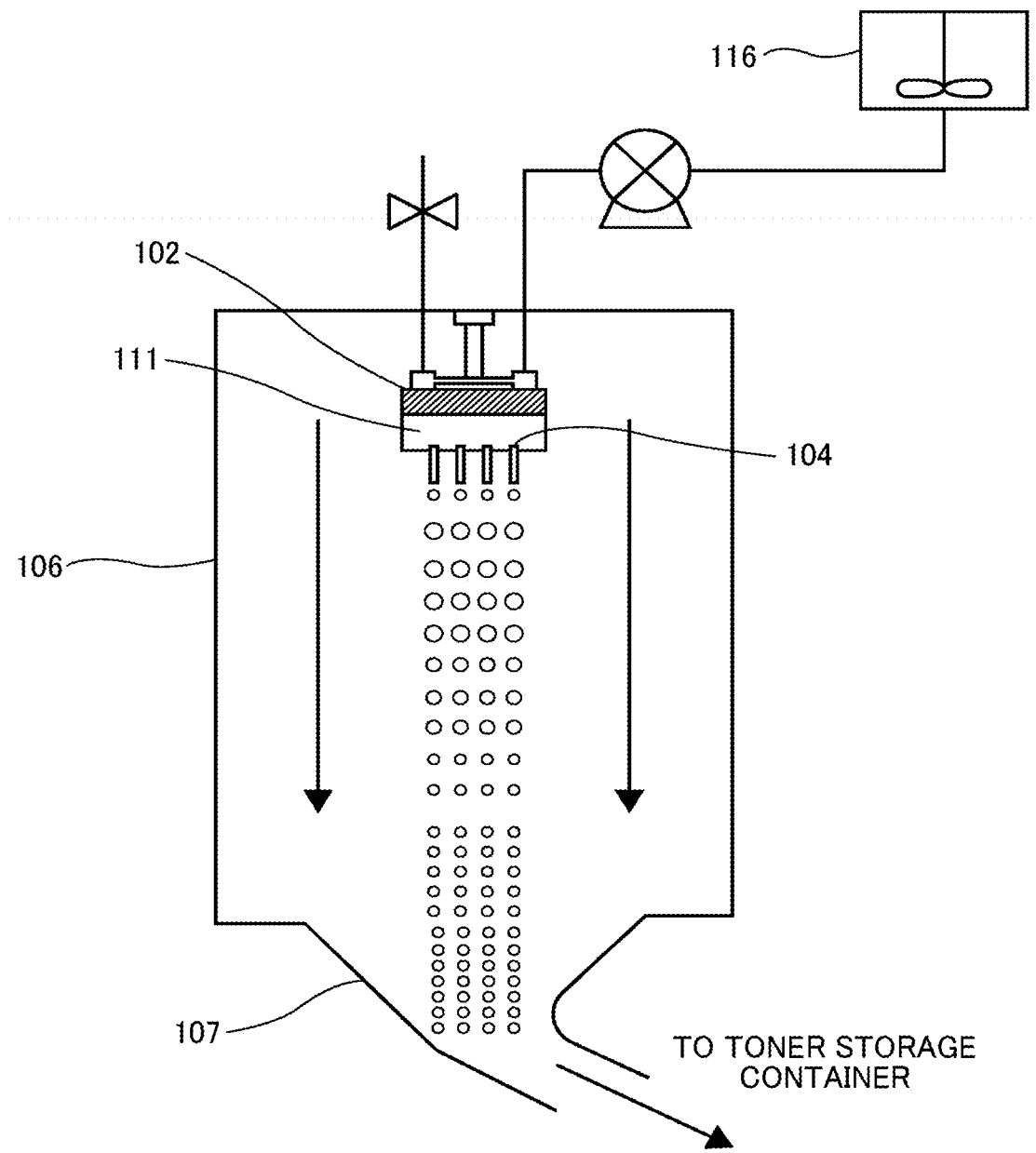
FIG. 5 is a schematic diagram illustrating a particle-producing apparatus according to another embodiment of the present invention.
Figure 6:
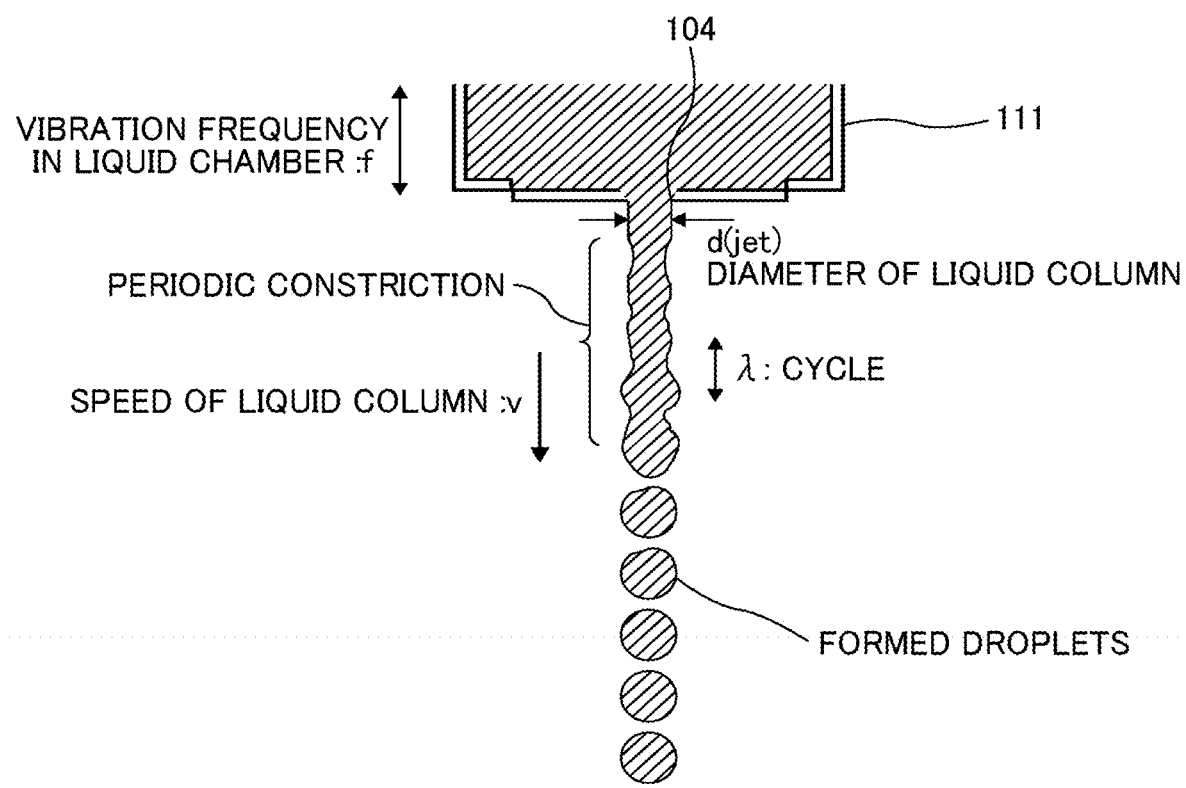
FIG. 6 is a schematic diagram illustrating a droplet-discharging device using a constricted part-generating device, used in the particle-producing apparatus illustrated in FIG. 5.

Next, for another example of the particle-producing apparatus used in the particle-producing method of the present disclosure, a particle-producing apparatus described in JP-2007-199463-A will be described. As illustrated in FIG. 5 and FIG. 6, this particle-producing apparatus includes a liquid-storing unit 111 for storing at least a particle raw material fluid, a vibration device 102, and through holes 104. The particle raw material fluid to be discharged from the through holes 104 is quantitatively supplied to the liquid-storing unit 111, and quantitatively discharged from the through holes 104 to form a liquid column. In this production apparatus, the number X of the vibration devices and the number Y of the through holes satisfy $10*X \leq Y \leq 10000*X$. The vibration device is in contact with a part of the liquid-storing unit to excite vibration of the particle raw material fluid through liquid-storing unit.

The particle raw material fluid is made into droplets by this excitation, and the droplets are dried into solid particles.

As illustrated in FIG. 5, a preferable particle-producing apparatus includes at least the liquid-storing unit 111 for storing at least the particle raw material fluid, the vibration device 102, a support device for holding the vibration device, and the plurality of through holes 104, as the droplet-forming device. Preferably, the apparatus further includes a liquid-supplying device 116 for quantitatively supplying the particle raw material fluid to be discharged from the through holes 104 to the liquid-storing unit 111 and quantitatively discharging the particle raw material fluid from the through holes, and a solvent-removing equipment and a particle-collecting unit 107 as a particle-forming device 106.

Figure 7:
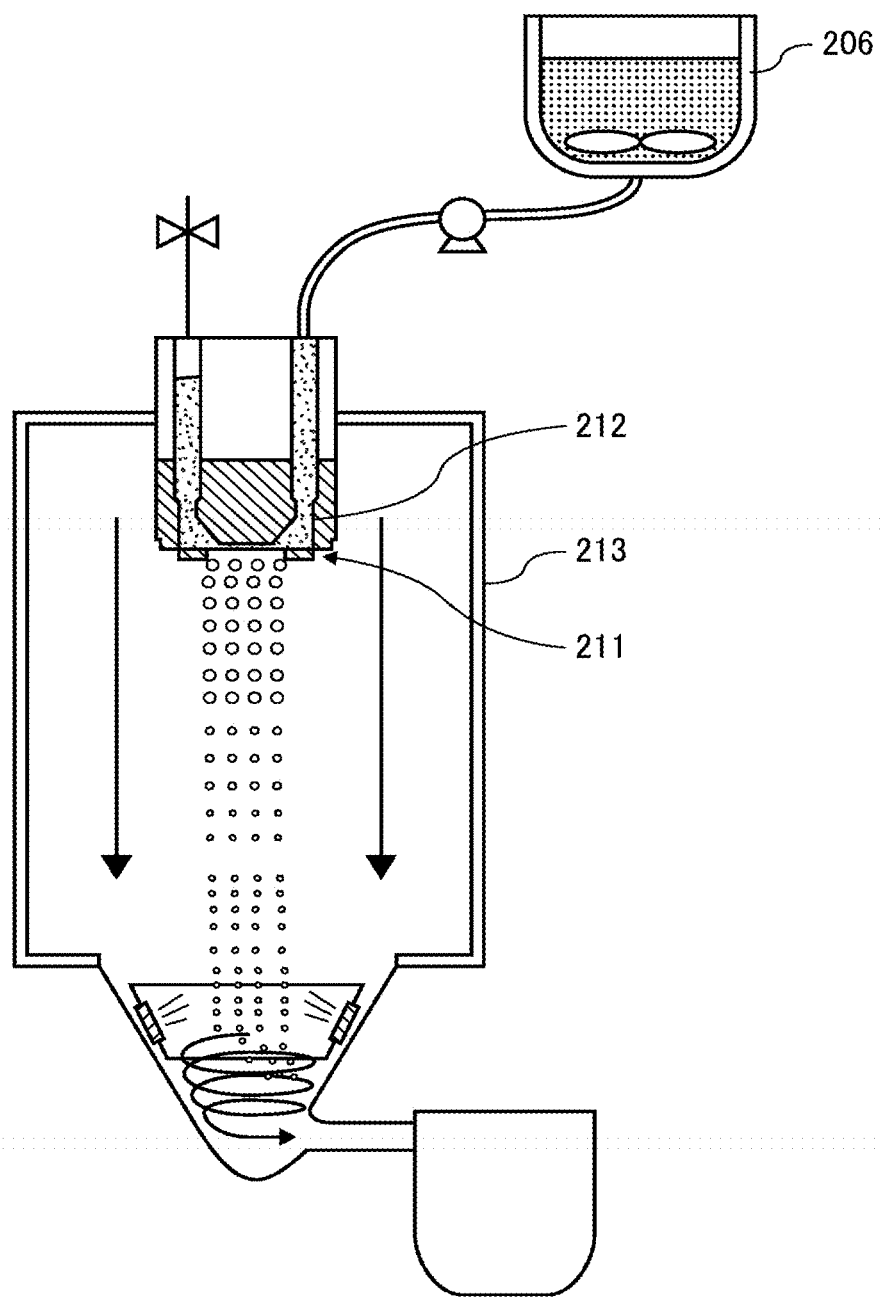
FIG. 7 is a schematic diagram illustrating a particle-producing apparatus according to another embodiment of the present invention.
Figure 8A:
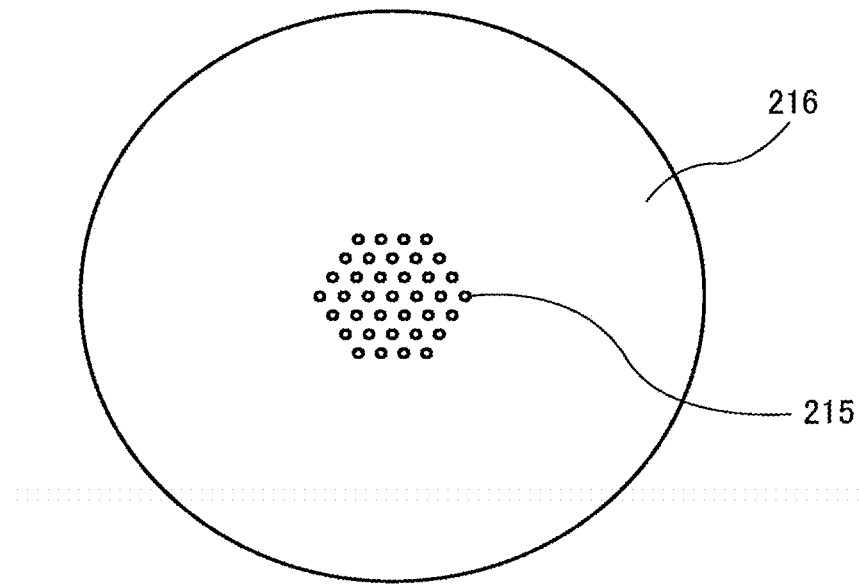
FIG. 8A is a plane view of a droplet-discharging device using a nozzle-vibrating device, used in the particle-producing apparatus illustrated in FIG. 7.
Figure 8B:
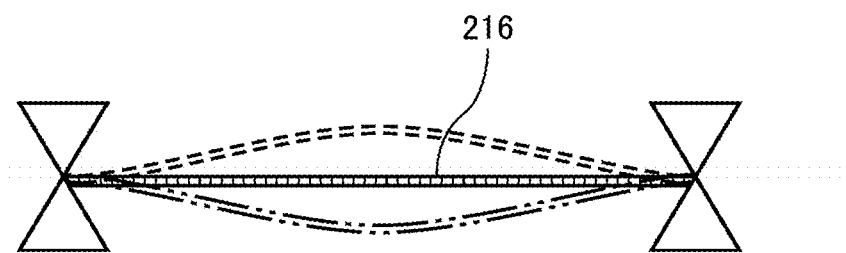
FIG. 8B is a side view of the droplet-discharging device using the nozzle-vibrating device, used in the particle-producing apparatus illustrated in FIG. 8.

In addition, another example of the particle-producing apparatus used in the particle-producing method of the present disclosure is a particle-producing apparatus described in JP-2008-292976-A. As illustrated in FIG. 7, FIG. 8A and FIG. 8B, this particle-producing apparatus is configured to conduct: a periodic droplet-forming step in which at least the particle raw material fluid is periodically made into droplets by being discharged from a plurality of nozzles 215 formed on a thin film 216, whereby a droplet-forming device 212 including an annular vibration-generating device 211 that is disposed on a periphery of a deformable area of the thin film 216 vibrates the thin film 216; and a particle-forming step in which the droplets of the discharged particle raw material fluid are solidified.

As illustrated in FIG. 7, a preferable particle-producing apparatus includes: the droplet-forming device 212 including the thin film 216 having a plurality of nozzles 215 and the annular vibration-generating device 211 which is disposed on the periphery of the deformable area of this thin film 216 and vibrates the thin film 216; a liquid-storing unit 206 for supplying at least the particle raw material fluid to this droplet-forming device 212; and a particle-forming device 213 for solidifying the droplets of the particle raw material fluid, which has been periodically formed into droplets and discharged from the plurality of nozzles 215 of the droplet-forming device 212, to form particles.

(Particle)

The particle of the present disclosure contains a physiologically active substance and a polymer. The content of the physiologically active substance in the particle is 25% by mass or more based on the mass of the particle, and the particle has a volume average particle diameter (Dv) of 12 µm to 100 µm, and a particle size distribution (i.e., a ratio of volume average particle diameter (Dv) to number average particle diameter (Dn)) of 1.00 to 1.50. The particle further optionally contains other components.

The particle of the present disclosure can be suitably produced by the particle-producing method of the present disclosure.

Since the particle of the present disclosure has a volume average particle diameter (Dv) of 12 µm to 100 µm and a particle size distribution (volume average particle diameter (Dv)/number average particle diameter (Dn)) of 1.00 to 1.50, the sustained releasability of the physiologically active substance in the particle can be highly controlled for medical applications and the like.

—Physiologically Active Substance—

The physiologically active substance is not particularly limited, and can be appropriately selected depending on the intended purpose. Examples of the physiologically active substance include, but are not limited to, a pharmaceutical compound, a functional food compound, and a functional cosmetic compound. When the physiologically active substance in the particle is a solid dispersion, the physiologically active substance is uniformly dispersed in a state of fine particles in the particle.

—Pharmaceutical Compound—

The pharmaceutical compound to be used for medicines is not particularly limited as long as the pharmaceutical compound achieves a form of a functional particle or a pharmaceutical composition, and can be appropriately selected depending on the intended purpose.

Specifically, for example, a slightly water-soluble compound applied to a solid dispersion can have an improved bioavailability even in a case of oral administration or the like, by producing the particle using the particle-producing method of the present disclosure described below.

The slightly water-soluble compound refers to a compound having a log P value of a water/octanol distribution coefficient of 3 or higher, and the water-soluble compound refers to a compound having a log P value of a water/octanol distribution coefficient of lower than 3. The water/octanol distribution coefficient can be measured according to JIS (Japanese Industrial Standards) Z 7260-107 (2000) Shake-flask method. In addition, the pharmaceutical compound includes any form such as a salt and a hydrate as long as the compound is effective as a medicine.

The water-soluble compound is not particularly limited, and can be appropriately selected depending on the intended purpose. Examples of the water-soluble compound include, but are not limited to, abacavir, acetaminophen, aciclovir, amiloride, amitriptyline, antipyrine, atropine, buspirone, caffeine, captopril, chloroquine, chlorpheniramine, cyclophosphamide, desipramine, diazepam, diltiazem, diphenhydramine, disopyramide, doxin, doxycycline, enalapril, ephedrine, ethambutol, ethynyl estradiol, fluoxetine, imipramine, clomipramine, glucose, ketorol, ketoprofen, labetalol, levodopa, levofloxacin, metoprolol, metronidazole, midazolam, minocycline, misoprostol, metformin, nifedipine, phenobarbital, prednisolone, promazine, propranolol, quinidine, rosiglitazone, salicylic acid, theophylline, valproic acid, verapamil, zidovudine, and calcitonin. These may be used alone or in combination.

The slightly water-soluble compound is not particularly limited, and can be appropriately selected depending on the intended purpose. Examples of the slightly water-soluble compound include, but are not limited to, griseofulvin, itraconazole, norfloxacin, tamoxifen, cyclosporine, glibenclamide, troglitazone, nifedipine, phenacetin, phenytoin, digitoxin, nilvadipine, diazepam, chloramphenicol, indomethacin, nimodipine, dihydroergotoxine, cortisone, dexamethasone, naproxen, tulobuterol, beclomethasone propionate, fluticasone propionate, pranlukast, tranilast, loratidine, tacrolimus, amprenavir, bexarotene, calcitrol, clofazimine, digoxin, doxercalciferol, dronabinol, etoposide, isotretinoin, lopinavir, ritonavir, progesterone, saquinavir, sirolimus, tretinoin, valproic acid, amphotericin, fenoldopam, melphalan, paricalcitol, propofol, vonconazole, ziprasidone, docetaxel, haloperidol, lorazepam, teniposide, testosterone, valrubicin, quercetin, and allopurinol. These may be used alone or in combination. Especially, cyclosporine and tranilast are preferable, and cyclosporine is more preferable.

A content of the pharmaceutical compound is preferably 5% by mass to 95% by mass, more preferably 5% by mass to 50% by mass based on the total mass of the particle according to the present embodiment. When the content of the pharmaceutical compound is 5% by mass to 95% by mass, the dose of the pharmaceutical compound as a pharmaceutical composition is appropriate and the pharmaceutical components can be easily re-dispersed in water by the action of the pharmaceutical compound, which is advantageous.

—Functional Food Compound—

The functional food compound is not particularly limited, and can be appropriately selected depending on the intended purpose. Examples of the functional food compound include, but are not limited to, vitamin A, vitamin D, vitamin E, lutein, zeaxanthin, lipoic acid, flavonoid, and fatty acid (e.g. omega-3 fatty acid, omega-6 fatty acid). These may be used alone or in combination.

—Functional Cosmetic Compound—

The functional cosmetic compound is not particularly limited, and can be appropriately selected depending on the intended purpose. Examples of the functional cosmetic compound include, but are not limited to, an alcohol, a fatty alcohol, a polyol, an aldehyde, an alkanolamine, an alkoxylated alcohol (e.g. a polyethylene glycol derivative of an alcohol or a fatty alcohol), an alkoxylated amide, an alkoxylated amine, an alkoxylated carboxylic acid, a salt-containing amide (e.g. a ceramide), an amine, an amino acid including a salt and an alkyl-substituted derivative thereof, an ester, an alkyl-substituted and acyl derivative, a polyacrylic acid, an acrylamide copolymer, an adipic acid copolymer, an aminosilicone, a biological polymer and a derivative thereof, a butylene copolymer, a carbohydrate (e.g. a polysaccharide, a chitosan, and a derivative thereof), a carboxylic acid, a carbomer, an ester, an ether, and a polymer ether (e.g. a PEG derivative, a PPG derivative), a glyceryl ester and a derivative thereof, a halogen compound, a salt-containing heterocyclic compound, a hydrophilic colloid as well as a derivative thereof including a salt and a gum (e.g. a cellulose derivative, gelatin, xanthan gum, natural rubber), an imidazoline, an inorganic substance (e.g., clay, $TiO_2$, ZnO), a ketone (e.g. camphor), an isethionate, a lanolin and a derivative thereof, an organic salt, a salt-containing phenol (e.g. a paraben), a phosphorus compound (e.g. a phosphoric acid derivative), a polyacrylate and an acrylate copolymer, a protein and an enzyme derivative thereof (e.g. collagen), a salt-containing synthetic polymer, a siloxane and a silane, a sorbitan derivative, a sterol, a sulfonic acid and a derivative thereof, and a wax. These may be used alone or in combination.

A particle containing these pharmaceutical compounds, functional food compounds, or functional cosmetic compounds can be suitably used for a pharmaceutical, a food, or a cosmetic.

—Pharmaceutical—

The pharmaceutical contains the pharmaceutical compound, and furthermore optionally contains a dispersant, an additive, and other components.

The pharmaceutical is not particularly limited, and can be appropriately selected depending on the intended purpose. Examples of the pharmaceutical include, but are not limited to, those in a solid dosage form such as a tablet, a capsule, and a suppository; an intranasal or intrapulmonary aerosol; and a liquid formulation such as an injection, an eye drop, an ear drop, and an oral agent.

In addition, by mixing a dispersant, an additive or the like, the particle can be produced as a functional particle having a functionality or a pharmaceutical composition.

The functional particle is not particularly limited, and can be appropriately selected depending on the intended purpose. Examples of the functional particle include, but are not limited to, an immediate release particle, a sustained release particle, a pH-dependent release particle, a pH-independent release particle, an enteric coated particle, a controlled release coated particle, and a nanocrystal-containing particle. These may be used alone or in combination.

The pharmaceutical composition is not particularly limited, and can be appropriately selected depending on the intended purpose. Examples of the pharmaceutical composition include, but are not limited to, a colic delivery preparation, a lipid microsphere preparation, a dry emulsion preparation, a self-emulsifying preparation, a dry syrup, a transnasal powder preparation, a transpulmonary powder preparation, a wax matrix preparation, a hydrogel preparation, a polymeric micelle preparation, a mucoadhesive preparation, a gastric floating preparation, a liposome preparation, and a solid dispersion preparation. These may be used alone or in combination.

The pharmaceutical may be a pharmaceutical composition or a drug substance.

—Food—

The food contains the functional food compound, and furthermore optionally contains a dispersant, an additive, and other components.

The food is not particularly limited, and can be appropriately selected depending on the intended purpose. Examples of the food include, but are not limited to, frozen desserts such as ice cream, ice sherbet, and shaved ice; noodles such as buckwheat noodles, Japanese wheat noodle, gelatin noodle, Chinese meat dumpling sheet, Chinese steamed meat dumpling sheet, Chinese noodle, and instant noodle; confectioneries such as candy, gum, chocolate, tablet candy, snack, biscuit, jelly, jam, cream, baked sweet, and bread; marine products such as crab, salmon, clam, tuna, sardine, shrimp, bonito, mackerel, whale, oyster, saury, squid, ark shell, scallop, abalone, sea urchin, salmon roe, and Japanese ormer; processed marine and meat products such as boiled fish paste, ham and sausage; dairy products such as processed milk and fermented milk; oils and fats, and oil and fat processed foods such as salad oil, tempura oil, margarine, mayonnaise, shortening, whipped cream, and dressing; seasonings such as sauce, and mop sauce; retort-pouch foods such as curry, stew, rice bowl topped with chicken and egg, rice porridge, rice gruel, Chinese rice bowl, rice bowl topped with pork cutlet and egg, rice bowl topped with tempura, rice bowl topped with eel, hashed meat with rice, Japanese hotchpotch, Sichuan-style soybean curd, rice bowl topped with beef, meat sauce, egg soup, omelet rice, Chinese meat dumpling, Chinese steamed meat dumpling, hamburg steak, and meatball; and health foods and nutritional supplements in various forms.

—Cosmetic—

The cosmetic contains the functional cosmetic compound, and furthermore optionally contains a dispersant, an additive, and other components.

The cosmetic is not particularly limited, and can be appropriately selected depending on the intended purpose. Examples of the cosmetic include, but are not limited to, a skin care cosmetic, a makeup cosmetic, a hair care cosmetic, a body care cosmetic, and a fragrance cosmetic.

The skin care cosmetic is not particularly limited, and can be appropriately selected depending on the intended purpose. Examples of the skin care cosmetic include, but are not limited to, a cleansing composition for removing makeup, a facial cleanser, a milky lotion, a lotion, an essence, a skin moisturizer, a facial mask, and a shaving cosmetic (e.g. shaving foam, preshave lotion, aftershave lotion).

The makeup cosmetic is not particularly limited, and can be appropriately selected depending on the intended purpose. Examples of the makeup cosmetic include, but are not limited to, a foundation, a lipstick, and a mascara.

The hair care cosmetic is not particularly limited, and can be appropriately selected depending on the intended purpose. Examples of the hair care cosmetic include, but are not limited to, a hair shampoo, a hair rinse, a hair conditioner, a hair treatment, and a hairstyling product (e.g. hair gel, hair lotion, hair liquid, hair mist).

The body care cosmetic is not particularly limited, and can be appropriately selected depending on the intended purpose. Examples of the body care cosmetic include, but are not limited to, a body soap, a sunscreen cosmetic, and a massage cream.

The fragrance cosmetic is not particularly limited, and can be appropriately selected depending on the intended purpose. Examples of the fragrance cosmetic include, but are not limited to, a scent (e.g. perfume, parfum), an eau de parfum (e.g. perfume colon), an eau de toilette (e.g. perfume de toilette, parfum de toilette), and an eau de cologne (e.g. cologne, fresh cologne).

—Polymer—

The polymer is used for controlling a discharge rate of the physiologically active substance by adsorbing the physiologically active substance to the polymer, and for encapsulating the physiologically active substance with a capsule made of the polymer, and other purposes.

The polymer may be any polymer as long as the polymer is slightly soluble or insoluble in water and has biocompatibility, and can be appropriately selected depending on the intended purpose. Examples of the polymer include, but are not limited to, biodegradable polymers such as poly-fatty acid ester, poly-α-cyanoacrylate, poly-β-hydroxybutyric acid, polyalkylene oxalate, polyorthoester, polyorthocarbonate, other polycarbonates, and polyamino acid. These may be used alone or in combination.

Examples of the poly-fatty acid ester include, but are not limited to, polylactic acid, polyglycolic acid, and polymalic acid.

As the poly-fatty acid ester, a synthesized product, or a commercially available product may be appropriately used.

Examples of the commercially available product of the poly-fatty acid ester include, but are not limited to, PLGA-7510 (lactic acid/glycolic acid copolymer, manufactured by Wako Pure Chemical Industries, Ltd.).

Examples of other biocompatible polymers further include, but are not limited to, polystyrene, polyurethane, polyvinyl acetate, polyvinyl alcohol, polyacrylamide, polyacrylic acid, polymethacrylic acid, acrylic acid/methacrylic acid copolymer, polyamino acid, silicone polymer, dextran stearate, maleic anhydride-based copolymer, ethylcellulose, acetylcellulose, nitrocellulose, nylon, and tetron. These may be used alone or in combination.

—Other Component—

Other components are not particularly limited, and can be appropriately selected depending on the intended purpose. Examples of other components include, but are not limited to, water, the excipient, the flavor improver, the disintegrator, the fluidizer, the adsorbent, the lubricant, the odor improver, the surfactant, the fragrance, the colorant, the antioxidant, the masking agent, the antistatic agent, and the wetting agent, described above. These may be used alone or in combination. Details of these components are spared because they are the same as described above.

<Volume Average Particle Diameter (Dv) of Particle>

The particle preferably has a volume average particle diameter (Dv) of 12 μm to 100 μm, and more preferably 15 μm to 30 μm.

When the particle has a volume average particle diameter (Dv) of 12 μm to 100 μm, the particle can retain the physiologically active substance which can be sustainably released for an extended period of time.

In addition, when the particle has a volume average particle diameter (Dv) of 12 μm or greater, the polymer can appropriately retain the physiologically active substance, and thereby the initial burst can be prevented, and a long-term sustained release effect can be exhibited.

In addition, when the particle has a volume average particle diameter (Dv) of 100 μm or smaller, the diameter is adequate as the size of the particle to be administered into a body, and energy requisite for drying the droplets during the particle production can be saved.

—Number Average Particle Diameter (Dn) of Particle—

The particle preferably has a number average particle diameter (Dn) of 12 μm to 100 μm, and more preferably 12 μm to 30 μm. When the particle has a number average particle diameter (Dn) of 12 μm to 100 μm, an amount of the eluted physiologically active substance per a unit time can be increased, because a surface area of the particle per a unit mass can be increased.

In addition, when the particle has a number average particle diameter (Dn) of 12 μm or greater, the sustained releasability can be exhibited for an extended period of time, because the particle can contain the polymer in an amount sufficient to adsorb the physiologically active substance.

<Particle Size Distribution (Volume Average Particle Diameter (Dv)/Number Average Particle Diameter (Dn))>

A particle size distribution is a value obtained by dividing the volume average particle diameter (Dv) by the number average particle diameter (Dn), and is preferably 1.00 to 1.50, more preferably 1.00 to 1.20, and even more preferably 1.00 to 1.10.

When the particle has a particle size distribution of 1.00 to 1.50, the size of the particle is uniform, and contents of the physiologically active substance and the polymer in each particle are uniform, and thereby the sustained releasability can be highly controlled.

The volume average particle diameter (Dv), the number average particle diameter (Dn), and the particle size distribution (Dv/Dn) of the particle can be measured using a laser diffraction/scattering type particle size distribution measuring apparatus (apparatus name: Microtrac MT 3000 II, manufactured by MicrotracBEL Corp.).

<Content of Physiologically Active Substance in Particle>

A content of the physiologically active substance in the particle is preferably 25% by mass or more, more preferably 25% by mass to 75% by mass, in terms of the dried particle.

In the particle-producing method and the particle-producing apparatus of the present disclosure, the content of the physiologically active substance in the particle can be controlled by adjusting the formulation of the mixed liquid, and particle having a higher ratio of the physiologically active substance can be produced compared to other production methods. For example, the content of the physiologically active substance can be 15% by mass or more, or 20% by mass or more in terms of the dried particle. The content can be controlled depending on the required sustained releasability, and particularly when the content of the physiologically active substance in the particle is 25% by mass or more, the physiologically active substance can be stably eluted for an extended period of time.

In addition, when the content of the physiologically active substance in the particle is 25% by mass to 75% by mass, the sustained releasability can be accurately controlled while increasing the content of the physiologically active substance in the particle.

The particle of the present disclosure contains the physiologically active substance and the polymer. The content of the physiologically active substance is 25% by mass or more based on the mass of the particle, and the particle has a volume average particle diameter (Dv) of 12 µm to 100 µm, and a particle size distribution (volume average particle diameter (Dv)/number average particle diameter (Dn)) of 1.00 to 1.50, so that the sustained releasability can be accurately controlled, and the particle can contain a high concentration of physiologically active sub stance.

Next, the relationship between the sustained releasability of the particle and the particle size distribution (volume average particle diameter (Dv)/number average particle diameter (Dn)) will be explained with reference to FIG. 9 to FIG. 12.

Figure 9:
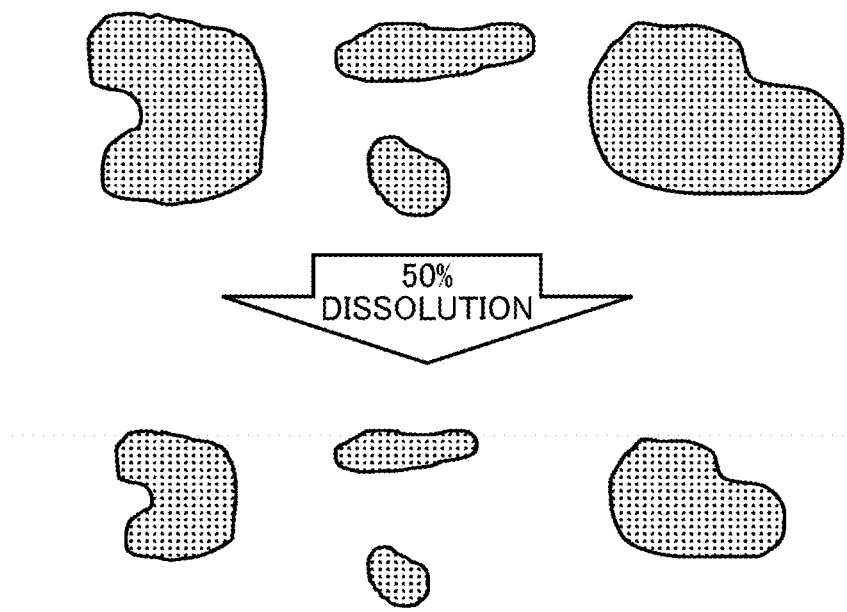
FIG. 9 is a schematic diagram illustrating a case in which 50% of a particle having a wide particle size distribution (Dv/Dn≠1) is dissolved.
Figure 10:
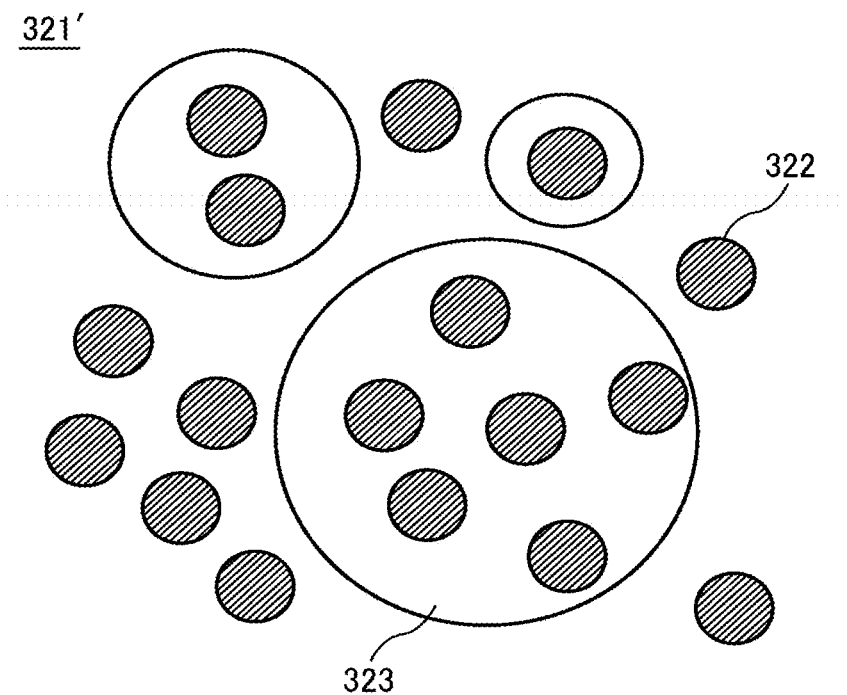
FIG. 10 is a schematic diagram illustrating a particle produced by spray drying.
Figure 11:
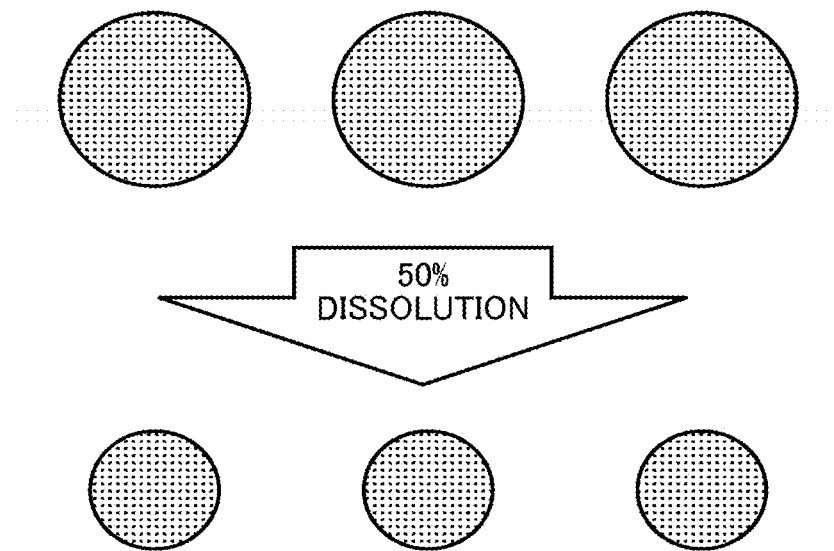
FIG. 11 is a schematic diagram illustrating a case in which 50% of a particle having a narrow particle size distribution (Dv/Dn=1) is dissolved.
Figure 12:
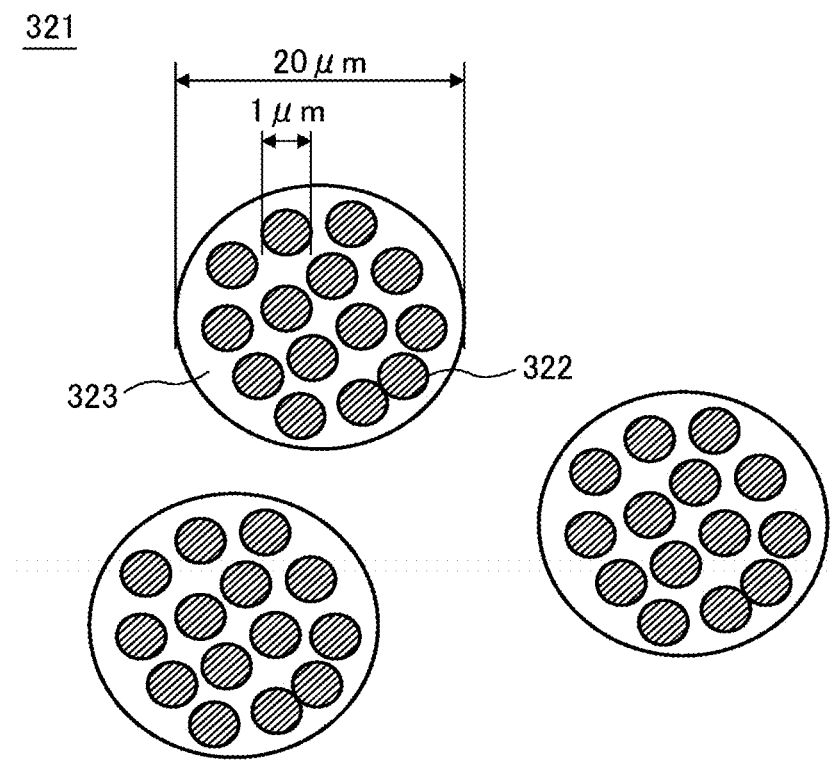
FIG. 12 is a schematic diagram illustrating the particle produced by the particle-producing method according to an embodiment of the present invention.

FIG. 9 is a schematic diagram illustrating an example of a case in which 50% of the particle having a wide particle size distribution (Dv/Dn≠1) is dissolved. FIG. 10 is a schematic diagram illustrating the particle produced by spray drying. FIG. 11 is a schematic diagram illustrating an example of a case in which 50% of the particle having a narrow particle size distribution (Dv/Dn=1) is dissolved. FIG. 12 is a schematic diagram illustrating an example of the particle produced by the particle-producing method of the present disclosure.

FIG. 9 is a diagram illustrating a state that the particle size distribution is wide, i.e. a state that the size of each particle is ununiform. When the size of each particle is ununiform as illustrated in FIG. 9, the surface area of each particle varies, thus the elution rate of the physiologically active substance in each particle is ununiform, and the sustained releasability of the particle cannot be controlled.

As a specific example of FIG. 9, FIG. 10 presents an example of a particle 321' produced by the spray drying. As illustrated in FIG. 10, use of the spray drying may bring not only a situation that the size of each particle is ununiform, but also a situation that the physiologically active substance 322 is exposed without being encapsulated in the polymer 323. Consequently, the particle 321' having a wide particle size distribution may cause an initial burst during oral ingestion. In addition, the sustained releasability achieved by the polymer 323 containing a requisite amount of physiologically active substance 322 cannot be obtained.

In addition, FIG. 11 is a diagram illustrating a state that the particle size distribution is narrowed (Dv/Dn=1), i.e. the size of each particle is substantially uniform.

The elution rate of the physiologically active substance in each particle can be equalized by making the sizes of each particle substantially uniform as illustrated ion FIG. 11, so that the sustained releasability can be highly controlled.

As a specific example of FIG. 11, FIG. 12 presents an example of a particle 321 produced by the particle-producing method of the present disclosure. As illustrated in FIG. 12, since each particle of the present disclosure has the uniform particle size and the great particle diameter, the physiologically active substance 322 is encapsulated in the polymer 323, and furthermore uniformly dispersed in the particle, so that the sustained releasability can be secured, and the sustained releasability can be controlled with high precision.

EXAMPLES

Hereinafter, the present invention will be explained with reference to Examples. However, the present invention is not limited to Examples in any way.

Example 1

—Production of Particle by Volume-Changing Device (Piezo Method)—
<Preparation of Mixture A>

In 40 parts by mass of methanol (manufactured by Wako Pure Chemical Industries, Ltd.), 8 parts by mass of clomipramine hydrochloride (manufactured by Wako Pure Chemical Industries, Ltd.) was dissolved, 48 parts by mass of the resulting solution, 12 parts by mass of lactic acid/glycolic acid copolymer (trade name: PLGA-5010, manufactured by Wako Pure Chemical Industries, Ltd.), and 40 parts by mass of acetone (manufactured by Wako Pure Chemical Industries, Ltd.) were mixed and stirred using a stirrer (apparatus name: magnetic stirrer, manufactured by AS ONE Corporation) at 1,000 rpm for 1 hour, and passed through a 1 µm filtration filter (trade name: Millex SLFA 05010, manufactured by Merck KGaA) to prepare a mixture A.

<Granulation of Particle 1>

The prepared mixture A was discharged in a form of droplets by a droplet-discharging apparatus (apparatus name: GEN 4, manufactured by Ricoh Co., Ltd.) illustrated in FIG. 1 and FIG. 3 under the following particle granulation condition, and the discharged droplets were dried to granulate a particle 1. Incidentally, the droplet-discharging apparatus employs an inkjet discharge method using a piezoelectric element as the discharge method.

—Particle Granulation Condition—
  Shape of discharge hole: true circle
  Diameter of discharge hole: 24
  Number of discharge holes: 384
  Dry air temperature: 50 degrees C.
  Apply voltage: 16.0 V
  Driving frequency: 32 kHz

Example 2

—Production of Particle by Volume-Changing Device (Piezo Method)—
<Preparation of Mixture B>

Metformin hydrochloride was pulverized by a ball mill until the volume average particle diameter was 1.5 μm, 8 parts by mass of the pulverized metformin hydrochloride (manufactured by Tokyo Chemical Industry Co., Ltd.), 12 parts by mass of lactic acid/glycolic acid copolymer (trade name: PLGA-7510, manufactured by Wako Pure Chemical Industries, Ltd.), and 80 parts by mass of acetone (manufactured by Wako Pure Chemical Industries, Ltd.) were mixed and stirred using a stirrer (apparatus name: magnetic stirrer, manufactured by AS ONE Corporation) at 1,000 rpm for 1 hour to prepare a mixture B. Since metformin hydrochloride is insoluble in acetone, metformin hydrochloride was dispersed in a solid state in the mixture B.
<Granulation of Particle 2>

A particle 2 was granulated in the same manner as in Example 1 except that the mixture A in Example 1 was changed to the mixture B.

Example 3

—Production of Particle by Constricted Part-Generating Device—
<Granulation of Particle 3>

The mixture A was supplied to the liquid-storing unit of the particle-producing apparatus illustrated in FIG. 5. The plate having through holes used was a nickel plate having a thickness of 20 μm on which ten true-circle through holes having an outlet diameter of 30 μm were made concentrically by removal machining (laser ablation) using mask reduction projection with a femtosecond laser. The area having the through holes was a square with sides of 0.5 mm. After preparing the mixture, droplets were formed under the following production condition, and then the droplets were dried and solidified to prepare a particle.
—Particle Production Condition—
Solid content in mixture: 10%
Dry air flow rate: 2.0 L/min in sheath, 3.0 L/min in apparatus
Temperature in apparatus: 65 degrees C.
Vibration frequency in common liquid chamber: 300 kHz

Example 4

—Production of Particle by Constricted Part-Generating Device—
<Granulation of Particle 4>

Particle 4 was produced in the same manner as in Example 3 except that the mixture A in Example 3 was changed to the mixture B.

Example 5

—Production of Particle by Nozzle-Vibrating Device—
<Method for Producing Particle 5>

The mixture A was supplied to the liquid-storing unit of the particle-producing apparatus illustrated in FIG. 7. The thin film used was a nickel plate with an outer diameter of 8 mm and a thickness of 20 μm on which true-circle discharge holes with a diameter of 30 μm were made by electroforming process. The discharge holes were provided in a staggered pattern only on a range of a circle with a diameter (φ) of 5 mm around the center of the thin film so that the distance between the discharge holes was 100 μm. The mixture A was discharged in a form of droplets under the following production condition, and then the droplets were dried and solidified to prepare a particle.
—Particle Production Condition—
Solid content in mixture: 10%
Dry air flow rate: 2.0 L/min in sheath, 3.0 L/min in apparatus
Temperature in apparatus: 65 degrees C.
Vibration frequency in common liquid chamber: 100 kHz

Example 6

—Production of Particle by Nozzle-Vibrating Device—
<Granulation of Particle 6>

A particle 6 was produced in the same manner as in Example 5 except that the mixture A in Example 5 was changed to the mixture B.

Comparative Example 1

—Production of Particle by Spray Drying—
<Granulation of Particle 7>
—Production of Particle by Spray Drying—

The mixture A prepared in Example 1 was discharged in a form of droplets using a particle-producing apparatus (device name: 6552-1/8 JAC mini type, manufactured by SPRAYING SYSTEMS CO., JAPAN) by spray drying under the following condition, and dried to obtain a particle 7.
—Particle Production Condition—
Nozzle diameter: 0.5 mm
Air pressure: 0.1 MPa
Dry air temperature: 50 degrees C.

Comparative Example 2

—Production of Particle by Spray Drying—
<Granulation of Particle 8>

A particle 8 was produced in the same manner as in Comparative Example 1 except that the mixture A in Comparative Example 1 was changed to the mixture B.

Comparative Example 3

<Granulation of Particle 9>
—Production of Particle by in-Water Drying—

The mixture A prepared in Example 1 was discharged in a form of droplets into a water-containing beaker using a droplet-discharging apparatus (apparatus name: GEN 4, manufactured by Ricoh Co., Ltd.), so that the mixture A was emulsified in water. The resulting emulsion obtained by emulsifying the mixture A in water was centrifuged at 1,000 rpm in a centrifuge (apparatus name: CT6E, manufactured by Yamato Scientific co., ltd.) for 10 minutes to produce a particle 9.

Comparative Example 4

—Production of Particle by in-Water Drying—
<Granulation of Particle 10>

A particle 10 was produced in the same manner as in Comparative Example 3 except that the mixture A in Comparative Example 3 was changed to the mixture B.

Next, for particles 1 to 10 obtained in Examples 1 to 6 and Comparative Examples 1 to 4, "particle size distribution [volume average particle diameter (Dv)/number average particle diameter (Dn)]" and "physiologically active substance content (mass ratio)" were measured and evaluated in the following manner. The results are presented in Table 1.

<Particle Size Distribution [Volume Average Particle Diameter (Dv)/Number Average Particle Diameter (Dn)]>

The particle size distribution was measured using a laser diffraction/scattering type particle size distribution measuring apparatus (apparatus name: Microtrac MT 3000 II, manufactured by MicrotracBEL Corp.). The measurement/analysis conditions were set as follows.

—Measurement Condition for Particle Size Distribution—
Measurement mode: transmission mode
Particle refractive index: 1.40
Set Zero time: 10 seconds
Measurement time: 10 seconds The particle size distribution was evaluated according to the following evaluation criteria.

[Evaluation Criteria]
Good: $1.0 \leq (Dv)/(Dn) \leq 1.5$
Bad: $1.0 > (Dv)/(Dn)$ or $(Dv)/(Dn) > 1.5$ <Measurement of Physiologically Active Substance Content in Particle>

For measuring the content of the physiologically active substance in the particle, solutions prepared by dissolving the respective particles 1 to 10 in purified water (manufactured by Wako Pure Chemical Industries, Ltd.) were quantified by ultrahigh-performance liquid chromatography (manufactured by Waters Corporation) using a single quadrupole mass spectrometer (apparatus name: ACQUTTY SQD, manufactured by Waters Corporation) as a detector. Quantitative results were evaluated based on the following evaluation criteria.

[Evaluation Criteria]
Good: The mass ratio of the physiologically active substance is 25% or higher based on the mass of the particle
Bad: The mass ratio of the physiologically active substance is lower than 25% based on the mass of the particle volume-changing device to discharge droplets; and drying the discharged droplets to granulate a particle.

(2) The particle-producing method according to (1), wherein the physiologically active substance is dispersed in the liquid in the liquid-storing unit.

(3) The particle-producing method according to (1) or (2), wherein the volume-changing device is a piezoelectric element.

(4) The particle-producing method according to any one of (1) to (3), wherein the drying includes transporting the droplets with a transporting air flow to prevent coalescence of the droplets.

(5) The particle-producing method according to (4), wherein a transporting direction of the transporting air flow is substantially perpendicular to a direction of discharging the droplets.

(6) A particle comprising a physiologically active substance and a polymer, wherein a content of the physiologically active substance in the particle is 25% by mass or more based on the mass of the particle, wherein the particle has a volume average particle diameter (Dv) of 12 µm to 100 µm, and a particle size distribution (volume average particle diameter (Dv)/number average particle diameter (Dn)) of 1.00 to 1.50.

(7) The particle according to (6), wherein the physiologically active substance is a pharmaceutical compound.

(8) The particle according to (6) or (7), wherein the physiologically active substance is a solid dispersion.

(9) The particle according to any one of (6) to (8), wherein the physiologically active substance is in a state of fine particles in the particle.

(10) The particle according to any one of (6) to (9), wherein the polymer is slightly soluble or insoluble in water and is a biodegradable polymer.

(11) A particle-producing method comprising: discharging a liquid from discharge holes provided on a liquid-storing unit storing the liquid to make the liquid into droplets, the liquid containing a physiologically active substance and a polymer; and solidifying the droplets into a particle.

TABLE 1

| | | | | | | Evaluation results | | |
|---|---|---|---|---|---|---|---|---|
| | | Production Method | Volume average particle diameter (Dv) (µm) | Number average particle diameter (Dn) (µm) | Particle size distribution (Dv/Dn) | Mass ratio of physiologically active substance (%) | Volume average particle diameter (Dv) | Particle size distribution | Mass ratio of physiologically active substance (%) |
| Examples | 1 | Volume- | 16.80 | 15.94 | 1.05 | 40 | Good | Good | Good |
| | 2 | changing device | 17.45 | 16.35 | 1.07 | 40 | Good | Good | Good |
| | 3 | Constricted | 19.61 | 19.17 | 1.02 | 40 | Good | Good | Good |
| | 4 | part-generating device | 20.08 | 19.31 | 1.04 | 40 | Good | Good | Good |
| | 5 | Nozzle-vibrating | 20.03 | 16.25 | 1.23 | 40 | Good | Good | Good |
| | 6 | device | 19.78 | 15.48 | 1.28 | 40 | Good | Good | Good |
| Comparative | 1 | Spray drying | 16.52 | 6.02 | 2.74 | 40 | Good | Bad | Good |
| Examples | 2 | | 16.37 | 5.26 | 3.12 | 40 | Good | Bad | Good |
| | 3 | In-water drying | 14.14 | 12.87 | 1.10 | 10 | Good | Good | Bad |
| | 4 | | 13.37 | 10.62 | 1.26 | 10 | Good | Good | Bad |

Embodiments of the present invention provides the following items (1) to (22).

(1) A particle-producing method comprising: changing a volume of a liquid-storing unit storing a liquid containing a physiologically active substance and a polymer using a

(12) The particle-producing method according to (11), wherein a content of the physiologically active substance in the particle is 25% by mass or more based on the mass of the particle, and wherein the particle has a volume average particle diameter (Dv) of 12 µm to 100 µm, and a particle size distribution (volume average particle diameter (Dv)/number average particle diameter (Dn)) of 1.00 to 1.50.

(13) The particle-producing method according to (11) or (12), wherein the physiologically active substance is dispersed in the liquid in the liquid-storing unit.

(14) The particle-producing method according to any one of (11) to (13), wherein the discharging includes vibrating the liquid using a vibration device.

(15) The particle-producing method according to (14), wherein the vibration device is a piezoelectric element.

(16) The particle-producing method according to any one of (11) to (15), wherein the solidifying includes transporting the droplets with a transporting air flow to prevent coalescence of the droplets.

(17) The particle-producing method according to (16), wherein a transporting direction of the transporting air flow is substantially perpendicular to a discharging direction of the droplets.

(18) The particle-producing method according to any one of (11) to (17), wherein the physiologically active substance is a pharmaceutical compound.

(19) The particle-producing method according to any one of (11) to (18), wherein the physiologically active substance is a solid dispersion.

(20) The particle-producing method according to any one of (11) to (19), wherein the physiologically active substance is in a state of fine particles in the particle.

(21) The particle-producing method according to any one of (11) to (20), wherein the polymer is slightly soluble or insoluble in water and is a biodegradable polymer.

(22) A particle-producing apparatus comprising: a discharge device including a liquid-storing unit storing a liquid containing a physiologically active substance and a polymer, configured to discharge the liquid from discharge holes provided on the liquid-storing unit to make the liquid into droplets; and a solidification device configured to solidify the droplets into a particle, wherein a content of the physiologically active substance in the particle is 25% by mass or more based on the mass of the particle, wherein the particle has a volume average particle diameter (Dv) of 12 µm to 100 µm, and a particle size distribution (volume average particle diameter (Dv)/number average particle diameter (Dn)) of 1.00 to 1.50.

The particle-producing method according to any one of (1) to (5) and (11) to (21), the particle according to any one of (6) to (10), and the particle-producing apparatus according to (22) can solve the various problems art and achieve the object of the present invention.

Numerous additional modifications and variations are possible in light of the above teachings. It is therefore to be understood that, within the scope of the above teachings, the present disclosure may be practiced otherwise than as specifically described herein. With some embodiments having thus been described, it will be obvious that the same may be varied in many ways. Such variations are not to be regarded as a departure from the scope of the present disclosure and appended claims, and all such modifications are intended to be included within the scope of the present disclosure and appended claims.

The invention claimed is:

1. A particle-producing method, comprising:
discharging droplets of a liquid from discharge holes provided on a liquid-storing unit storing the liquid, the liquid containing a physiologically active substance dispersed in a solid state in the liquid in the liquid-storing unit, and the liquid containing a polymer, wherein the discharging of droplets is conducted with a droplet discharging device, and wherein said droplet discharging device is selected from the group consisting of a volume changing device, a constricted part generating device, and a nozzle vibration device; and
solidifying the droplets into solid particles so that the physiologically active substance in the particle is dispersed in a solid state,
wherein the particles have a volume average particle diameter ($D_v$) of 12 µm to 100 µm, and a particle size distribution, wherein the particle size distribution is volume average particle diameter ($D_v$)/number average particle diameter ($D_n$), of 1.00 to 1.50, and
the content of the physiologically active substance in the particles is 25% by mass or more based on the mass of the particle.

2. The particle-producing method according to claim 1, wherein the discharging includes vibrating the liquid using a vibration device.

3. The particle-producing method according to claim 2, wherein the vibration device is a piezoelectric element.

4. The particle-producing method according to claim 1, wherein the solidifying includes transporting the droplets with a transporting air flow to prevent coalescence of the droplets.

5. The particle-producing method according to claim 4, wherein a transporting direction of the transporting air flow is substantially perpendicular to a discharging direction of the droplets.

6. The particle-producing method according to claim 1, wherein the physiologically active substance is a pharmaceutical compound.

7. The particle-producing method according to claim 1, wherein the physiologically active substance is in a state of fine particles in a particle.

8. The particle-producing method according to claim 1, wherein the polymer is slightly soluble or insoluble in water and is a biodegradable polymer.

9. The particle-producing method according to claim 1, wherein the liquid is not subjected to a filtration process before discharging.

10. The particle-producing method of claim 8, wherein the pharmaceutical compound is selected from the group consisting of griseofulvin, itraconazole, norfloxacin, tamoxifen, cyclosporine, glibenclamide, troglitazone, nifedipine, phenacetin, phenytoin, digitoxin, nilvadipine, diazepam, chloramphenicol, indomethacin, nimodipine, dihydroergotoxine, cortisone, dexamethasone, naproxen, tulobuterol, beclomethasone propionate, fluticasone propionate, pranlukast, tranilast, loratidine, tacrolimus, amprenavir, bexarotene, calcitrol, clofazimine, digoxin, doxercalciferol, dronabinol, etoposide, isotretinoin, lopinavir, ritonavir, progesterone, saquinavir, sirolimus, tretinoin, valproic acid, amphotericin, fenoldopam, melphalan, paricalcitol, propofol, voriconazole, ziprasidone, docetaxel, haloperidol, lorazepam, teniposide, testosterone, valrubicin, quercetin, and allopurinol.

11. The particle-producing method of claim 10, wherein the pharmaceutical compound is cyclosporine.

12. The particle-producing method of claim 10, wherein the pharmaceutical compound is tranilast.

13. The particle-producing method of claim 6, wherein the pharmaceutical compound is selected from the group consisting of abacavir, acetaminophen, aciclovir, amiloride, amitriptyline, antipyrine, atropine, buspirone, caffeine, captopril, chloroquine, chlorpheniramine, cyclophosphamide, desipramine, diazepam, diltiazem, diphenhydramine, disopyramide, doxycycline, enalapril, ephedrine, ethambutol, ethynyl estradiol, fluoxetine, imipramine, clomipramine, clomipramine hydrochloride, glucose, ketorol, ketoprofen, labetalol, levodopa, levofloxacin, metoprolol, metronidazole, midazolam, minocycline, misoprostol, metformin, metformin hydrochloride, nifedipine, phenobarbital, prednisolone, prom azine, propranolol, quinidine, rosiglitazone, salicylic acid, theophylline, valproic acid, verapamil, zidovudine, and calcitonin.

14. The particle-producing method of claim 13, wherein the physiologically active substance is metformin or metformin hydrochloride.

15. The particle-producing method of claim 13, wherein the physiologically active substance is clomipramine or clomipramine hydrochloride.

* * * * *